US005506500A

United States Patent [19]
Krause et al.

[11] Patent Number: 5,506,500
[45] Date of Patent: * Apr. 9, 1996

[54] MAGNETIC PROPERTY CHARACTERIZATION SYSTEM EMPLOYING A SINGLE SENSING COIL ARRANGEMENT TO MEASURE BOTH AC SUSCEPTIBILITY AND DC MAGNETIZATION

[75] Inventors: John K. Krause; Victor Wang; Bradley C. Dodrill, all of Westerville, Ohio

[73] Assignee: Lake Shore Cryotronics, Inc., Westerville, Ohio

[*] Notice: The portion of the term of this patent subsequent to Mar. 11, 2012, has been disclaimed.

[21] Appl. No.: 231,063

[22] Filed: Apr. 22, 1994

Related U.S. Application Data

[63] Continuation of Ser. No. 853,400, Mar. 18, 1992, Pat. No. 5,311,125.

[51] Int. Cl.$^6$ ............ G01R 33/16; G01R 33/035; G01N 27/71; G01N 27/72
[52] U.S. Cl. ............ 324/201; 324/248; 324/262; 324/259; 324/224
[58] Field of Search ............ 324/201, 202, 324/244, 205, 248, 259, 204, 228, 260–262, 224, 226

[56] References Cited

U.S. PATENT DOCUMENTS

| | | |
|---|---|---|
| 2,975,360 | 3/1961 | Bell . |
| 3,454,875 | 7/1969 | Bol et al. . |
| 3,528,001 | 9/1970 | Yntema . |
| 3,665,297 | 5/1972 | Yates ............ 324/201 |
| 3,863,142 | 1/1975 | Werle . |
| 4,005,358 | 1/1977 | Foner . |
| 4,037,149 | 7/1977 | Foner . |
| 4,134,064 | 1/1979 | Jacobs et al. ............ 324/201 |
| 4,234,939 | 1/1981 | Grossman et al. ............ 324/201 |
| 4,238,734 | 12/1981 | Steingroever et al. . |
| 4,277,750 | 7/1981 | Bonnet et al. ............ 324/201 |
| 4,588,947 | 5/1986 | Ketchen ............ 324/201 |
| 4,849,695 | 7/1989 | Muller et al. . |
| 4,861,990 | 8/1989 | Coley . |
| 5,008,621 | 4/1991 | Jiles . |

OTHER PUBLICATIONS

B. D. Cullity, "Introduction to Magnetic Materials," pp. 65–66 (Addison–Wesley Publishing Company), (No Month) 1972.

Quantum Design Brochure, "MPMS2 AC Measurement and Field Cancelling Options," 2 pages, Aug. 1990.

R. B. Goldfarb, et al., "Alternating–Field Susceptometry and Magentic Susceptibility of Superconductors," pp. 1–32 (Plemum Press), May 1991.

J. Rebouillat, "High Resolution Automatic Magnetometer . . . Measurements," pp. 630–633 (IEEE Transactions on Magnetics), Sep. 1972.

Reference Material for Quantum Design's Seminar (Nov. 5–6, 1990 Seoul) Woo Sin Enterprise, Inc.

(List continued on next page.)

Primary Examiner—Sandra L. O'Shea
Assistant Examiner—Roger Phillips
Attorney, Agent, or Firm—Nixon & Vanderhye

[57] ABSTRACT

A coil arrangement having a primary and two balanced secondaries is used to measure ac susceptibility and, using sample movement, also to perform absolute dc moment measurements. Since the same coil arrangement is used for both AC and DC measurements, the measurements can be made successively within a cryogenic chamber without removing the sample. This is a big advantage, because the changed conditions associated with removing and replacing a sample between measurements can cause confusing, uncorrelated results. A high speed voltmeter is used to perform the signal analysis for the moment measurement. The system can be configured to yield high resolution dc moment measurements to 25 ppm and sensitivities to better than $5 \times 10^{-5}$ emu.

25 Claims, 12 Drawing Sheets

OTHER PUBLICATIONS

Rillo et al., "Multipurpose Cryostat for Low Temperature Magnetic and Electric Measurements of Solids," *Magnetic Susceptibility of Superconductors and Other Spin Systems,* Edited by R. A. Hein et al., Plenum Press, New York, pp. 1–24, May 1991.

C. Rillo, et al., "Multipurpose a.c. and d.c. Equipment . . . Measurements of Solids", May 1991.

H. Sasaki, "A Simple Precision Fluxmeter," pp. 100–102 (North–Holland Publishing Co.), Aug., 1969.

C. Edwards, et al., "A Magnetometer for Surface Flux Density Measurement in MPI," pp. 304–306 (British Journal of NDT), Sep. 1987.

P. Beckley, et al., "A Simplified electronic permeameter suitable for routine and standards use," pp. 379–384 (Measurement and Control), Oct., 1976.

L. F. Marinaccio, "Op amp converts DVM to fluxmeter," pp. 112–113 (Electronics), May, 1975.

E. G. DeMott, "Integrating fluxmeter with Digital Readout," pp. 269–271 (IEEE Transactions on Magnetics), Jun., 1970.

E. Seely, "Dowty RFL Offers the Only Digital Fluxmeter With IEEE–488 Bus Operation," (Dowty RFL Industries), Mar., 1986.

Lake Shore Cryotronics, Inc. Brochure, "AC Susceptibility Measurement—Its Purpose and Process," Nov. 1988.

C. Rillo, et al., "On the Sensitivity of High–TC Superconducting . . . Sensors," pp. 775–780 (Sensors and Actuators A–Physical), (No Month) 1991.

Bartolome, "Thermal, Magnetic, Magnetoelastic and Transport Characterization of Hard Magnetic Alloys," *Supermagnets, Hard Magnetic Materials,* Proceeedings of the NATO Advanced Study Institute on Supermagnets, Hard Magnetic Materials, II Ciocco, Italy Jun. 10–22, 1990, pp. 391–413, published by Kluwer Academic Publishers.

Broersma, "Inductance Apparatus for Diamagnetic Measurements," *The Review of Scientific Instruments,* vol. 20, No. 9, Sep. 1949, pp. 660–663.

Svendlindh, et al., "Static Scaling in an Amorphous Metallic Spin Glass," *Europhysics Letters,* 2 (10), pp. 805–812 (1986).

Butera, et al., "Apparatus for the Determination of Magnetothermodynamic Properties to High Fields at Low Temperatures utilizing a Superconducting Magnet," *The Review of Scientific Instruments,* vol. 39, No. 8, Aug. 1968, pp. 1138–1144.

Nave et al., "Micromagnetic susceptometer," *The Review of Scientific Instruments,* 51(5), pp. 591–596 (May 1980).

Hein et al., "Differential Paramagnetic Effect in Superconductors," *Physical Review,* vol. 121, No. 2, pp. 407–415 (Jul. 15, 1961).

Campbell et al., "Critical field measurements in sueprconductors using ac inductive techniques," *Review ofScientific Instruments,* 54 (9), pp. 1191–1198 (Sep. 1983).

MAGNETIC PROPERTY CHARACTERIZATION SYSTEM EMPLOYING A SINGLE SENSING COIL ARRANGEMENT TO MEASURE BOTH AC SUSCEPTIBILITY AND DC MAGNETIZATION

CROSS-REFERENCE TO RELATED APPLICATIONS

This application is a continuing application Ser. No. 07/853,400 filed 18 Mar. 1992 which issued on May 10, 1994 as U.S. Pat. No. 5,311,125.

FIELD OF THE INVENTION

The present invention relates to measuring the magnetic characteristics of a sample, and more particularly relates to measuring magnetic parameters using both AC and DC measuring techniques.

BACKGROUND AND SUMMARY OF THE INVENTION

AC susceptometry and DC magnetometry are two different widely used techniques for obtaining information about the magnetic characteristics of a sample. The following provides a brief background discussion of each of these well known techniques.

Briefly, in a typical dc magnetization measurement, a value for the magnetic moment m of the sample is measured for some applied dc field $H_{dc}$. The magnetic moment m is a bulk sample property and is a measure of the magnetic field generated by the sample itself. The dc or static "susceptibility" is determined by dividing the magnetization by the applied field ($x_{dc} = M/H_{dc}$). When comparing different materials (or samples of the same material having different sizes), the macroscopic quantity of interest is magnetization per unit volume (or per unit mass) of the sample.

Techniques for measuring the dc moment have long been commercialized in a variety of system products such as vibrating sample magnetometers (VSMs), force magnetometers, and SQUID magnetometers. The most commonly used dc magnetometers, such as the vibrating sample magnetometer (VSM) or SQUID magnetometer, generally use a detection coil to measure the change in magnetic flux due to the presence of a magnetized sample. If the sample does not have a permanent magnetic moment, an applied field is required.

FIG. 1 schematically illustrates a typical prior art commercial DC magnetometer. In many commercial DC magnetometers, a magnet 50 (e.g., an electromagnet or superconducting solenoid) is provided to apply a constant magnetic field $H_{dc}$ to the sample 52 in order to magnetize the sample to a magnetic moment (m). A detection coil 54 and associated detection circuit 56 are also provided. There is no output from the detection circuit 56 until there is a magnetic flux change within the detection coil 54 (Faraday's Law). The sample flux coupled to the detection coil 54 is commonly varied by moving the sample. In a VSM, the sample 52 is vibrated near detection coil 54. As the sample 52 moves, an ac signal is generated at a frequency determined by the sample oscillation. In a SQUID system, the sample 52 is simply passed through the detection coil 54. Typically, detection circuit 56 comprises a fluxmeter, lock-in amplifier, or SQUID electronics that is coupled to the detection coil 54 in order to measure the change in flux (i.e., the magnetic moment). A so-called "extraction technique" is known wherein the fluxmeter (detection circuit) 56 deflects in an amount proportional to the flux change (moment) as the sample is removed from the sensing coil. See Cullity, *Introduction to Magnetic Materials*, pages 61–81, and particularly, 65–66 (Addison-Wesley Publishing Co. 1972).

Traditionally, fluxmeters, which are essentially digital voltmeters, are used for measuring secondary coil output signals over time. However, most fluxmeters have a relatively low input impedance (which can present a problem when the sensing coils to be used have a large variable resistance). In addition, fluxmeters may present potential measuring difficulties in dealing with drifts and thermal emfs.

It is generally known to use an integrating digital voltmeter as a fluxmeter. It is apparently also known to use a digital voltmeter to measure voltages to indicate DC magnetization. For example, the Rebouillat and Sasaki references cited below each appear to teach using an integrating digital voltmeter as a fluxmeter for measuring magnetization. In addition, the Werle '142 patent (cited below) teaches a magnetic fluxmeter for measuring macro flux disturbances (e.g., caused by a ship passing by) which includes a digital voltmeter type indicator for indicating the level of a signal integrated in the analog domain. The Coley '990 patent (also cited below) appears to teach a digital voltmeter arrangement in his FIG. 4 tunneling susceptometer (see components 52–66).

When properly calibrated, the output from the VSM or SQUID magnetometer yields the value of the magnetic moment for the sample. With knowledge of the sample volume (V), the magnetization (M) can be determined. Magnetization and the dc susceptibility are thus derived quantities. Usually, the moment is measured as a function of field, and the materials' magnetization curve (i.e., m or M versus $H_{dc}$) is determined (see FIG. 2) by repeating the measurement for different values of $H_{dc}$. That is, in a dc magnetization measurement discrete points along some characteristic magnetization curve are measured. This permits measurement of several discrete points along the magnetization curve of the sample. If the magnetic field direction can be reversed, hysteresis curves can also be generated.

DC magnetization/susceptibility measurements are extremely useful (e.g., for high field studies and for measuring hysteresis curves). However, sometimes additional (or different) information about the magnetic properties of a sample is required that is not available from a DC type measurement. For example, there are instances in which "complex" (real and imaginary) magnetic susceptibility must be measured in order to provide more complete information about the magnetic characteristics (e.g., relaxation characteristics) of a sample. AC susceptometery provides certain information (e.g., information about such "complex" parameters) that is not available from DC magnetometry. Moreover, in the AC measurement, copper wound coils can be used to generate very small amplitude AC fields (e.g, >> 1 Oe) without complications arising from the remanent fields associated with iron-core or superconducting magnets. This means that the AC technique is very valuable in the study of low-field magnetic characteristics of a sample.

In addition, with the capability to vary the frequency of the drive field in an AC technique, the magnetodynamics of the magnetic system can also be studied. Further, since in the AC measurement the slope of the magnetization curve is being measured, non-linear magnetization and magnetic transitions are often best studied using an AC measurement.

AC susceptometry has thus been widely used for the characterization of magnetic materials for many years. However, prior to 1988, there was no serious commercial product available and ac susceptometer usage was almost universally "build your own" (so that, for example, many ac susceptometers were "laboratory assembled" using available components). Unlike the dc technique (where actual values for the magnetic moment m are measured), changes in m (i.e., Δm) are measured in the ac technique. Thus, the ac susceptibility gives an indication of the slope (dm/dH) of the magnetization curve. This is a fundamental difference between the ac and dc measurement techniques.

The discovery of high $T_c$ superconductors led to a rapid increase in interest in magnetic measurements. High $T_c$ materials are characterized by relatively small first critical fields, $H_{c1}$, and a small full penetration field, $H_p$. Therefore, a reliable low-field magnetization measurement technique is necessary for the full magnetic characterization of these materials.

In addition, the ac measurement can be used to differentiate between inter- and intragranular current coupling, and in determining the overall quality of a superconductor. An analysis of x" can provide information about the critical current density $J_c$ of these materials via the invocation of a suitable critical state model, and this sort of analysis has contributed to a better understanding of the mechanisms of superconductivity in these compounds.

An analysis of the complex susceptibility can also provide information about relaxational processes that may be occurring in the system under study. For example, it can be used to study spin-lattice relaxation phenomena in paramagnetic compounds, domain wall movement in metamagnetic systems, and has contributed to a better understanding of spin-glass systems.

Using the ac technique, the sample is generally centered within a detection coil and exposed to an applied AC magnetic field. The magnetic moment of the sample follows the applied field. The detection circuitry is generally balanced, with matched detection coils being provided in order to null out the changing flux due to the AC excitation. As a result, the detected change in flux is related only to the change in moment of the sample as it responds to the AC field.

Using well established principles of ac susceptometry, Lake Shore Cryotronics (the assignee of the present invention) introduced its 7000 line of ac susceptometers in the fall of 1988. FIG. 2A is a schematic block diagram showing this prior art ac susceptometer developed by Lake Shore. The basic principles of operation are described in Lake Shore's application note entitled "AC Susceptibility Measurement: Its Purpose and Process" (the disclosure of which is incorporated by reference herein for the purpose of providing discussion as to the state of the art). While no sample movement is required to perform AC susceptometery measurements, a motor and associated sample movement arrangement are provided in Lake Shore's ac susceptometer to move the sample in order to increase measurement accuracy and resolution.

Needless to say, much work has been done in the past in regard to magnetic characteristic measuring techniques. The following documents relate to techniques for measuring the magnetic characteristics of a sample:

Rillo et al, "Multipurpose a.c. and d.c. Equipment for Low Temperature Magnetic and Electric Measurements of Solids" (Abstract of paper presented at S ONR Workshop in May 1991);

U.S. Pat. No. 3,528,001—Yntema
U.S. Pat. No. 3,454,875—Bol et al
U.S. Pat. No. 4,861,990—Coley
U.S. Pat. No. 2,975,360—Bell
U.S. Pat. No. 4,037,149—Foner
U.S. Pat. No. 4,005,358—Foner
U.S. Pat. No. 4,238,734—Steingroever et al
U.S. Pat. No. 4,849,695—Muller et al
U.S. Pat. No. 5,008,621—Jiles
U.S. Pat. No. 3,863,142—Werle Goldfarb et al, "Alternating-Field Susceptometry and Magnetic Susceptibility of Superconductors" (Office of Naval Research Workshop on Magnetic Susceptibility of Superconductors and Other Spin Systems, Berkeley Springs, W.V. May 1991);

Rebouillat, "High Resolution Automatic Magnetometer Using a Superconducting Magnet: Application to High Field Susceptibility Measurements", *IEEE Trans. on Magnetics*, v. MAG-8, n. 3 pp. 630–33 (3 Sept. 1972);

Sasaki, "Simple Precision Fluxmeter", 76 *Nuclear Instruments and Methods* n. 1 pp. 100–2 (1 Dec 1969);

Edwards et al, "Magnetometer for Surface Flux Density Measurement in MPI", 29 *British Journal of Non-Destructive Testing* n. 5, pp. 304–306 (Sept. 1987);

Beckley et al, "Simplified Electronic Permeameter Suitable for Routine and Standards Use", 9 *Measurement and Control* n.10, p. T65–T70 (Oct. 1976);

Marinaccio, "Op Amp Converts DVM To Fluxmeter", 48 *Electronics* n.10, pp. 112–113 (May 15, 1975);

De Mott, "Integrating Fluxmeter with Digital Readout", *IEEE Journal on Magnetics* v. MAG-6 n.2 pp. 269–71 (2 Jun. 1970); and Press Release, "DOWTY RFL Offers The Only Digital Fluxmeter With IEEE-488 Bus Operation", Dowty RFL Industries, Boonton N.J. (Mar. 24, 1986).

Jiles teaches a measuring device capable of measuring various magnetic parameters (e.g., fluxmeter, gaussmeter, strain indicator), and uses the same overall transducer assembly for various measurements. The Dowty RFL press release describes a digital fluxmeter which measures "both flux density and total flux".

In addition, AC susceptometers, DC magnetometers and Vibrating Sample Magnetometers are commercially available from several companies. For example:

Quantum Design Inc. of San Diego, Calif. has been marketing a DC magnetometer since 1985, and as early as 1990 announced an option for making complex ac susceptibility measurements using elements of the SQUID detection system in its dc magnetometer. The means for making the ac measurements is not clear, nor has this group been able to qualify performance characteristics. In fact, it appears that no units have actually been delivered as of the filing date of the subject application.

Cryogenic Consultants Ltd., London England has been marketing, for approximately two years, a DC magnetometer employing a SQUID detection system. This device has no ac measurement capabilities. Cryogenic Consultants also markets a vibrating sample magnetometer.

Metronique Ingenierie of Le Bourget, France (no longer a going concern) introduced a SQUID (dc) Magnetometer in December 1989. They offered an ac measurement option which consisted of a separate set of sensing coils. The customer had to place a separate ac measurement insert into the dewar (refrigerator) system.

EG&G Princeton Applied Research (PARC), Princeton N.J., long ago introduced a vibrating sample magnetometer (VSM) that makes dc magnetization measurements. This instrument in found in many installations around the United States.

Princeton Measurements Corporation of Princeton New Jersey introduced an Alternating Gradient Force Magnetometer (AGFM) about two years ago—possibly to compete against VSMs and room temperature applications for SQUID magnetometers.

Phasetrack Instruments of Santa Clara, Calif. markets an ac susceptometer on a small scale. This instrument is not capable of making dc magnetization measurements.

See also generally the following papers relating to magnetic characteristic measurement: John K. Krause and Jeffrey R. Bergen, "Understanding magnetic measurement techniques," *Superconductor Industry*, vol. 3, no. 4, pp. 23–26, 1990;

Jiles, *Magnetization and Magnetic Materials,* pages 47–68 (Chapman & Hall 1991);

Goldfarb, "Thermoremanent magnetization and superparamagnetism in nickel-manganese alloys", Ph.D. dissertation (Colorado State University 1979);

Khoder et al, "Calibration constant calculations for Magnetic Susceptibility";

Couach et al, "Study of Superconductors by AC Susceptibility", *Cryogenics* Vol. 25, pp. 695–99 (1985);

Goldfarb et al, "Calibration of ac susCeptometers for cylindrical specimens", *Rev. Sci. Instrum.* vol. 55, pp. 761–64 (1984):

Zieba et al, "Superconducting Magnet Image Effects Observed With A Vibrating Sample Magnetometer", *Rev. Sci. Instrum.* Vol. 54, pp. 137–45 (1983); and Rillo et al, "On the Sensitivity of High-TC Superconducting Ceramics as Magnetic-Field Sensors", *Sensors and Actuators A-Physics,* Vol. 27, N1–3 pp. 775–80 (1991).

For some time there has been a desire in the field to develop a practical, cost-effective commercial instrument capable of providing both ac and dc measurement techniques. As mentioned above, for a complete study of the magnetic properties of at least certain samples it is desirable to perform both ac and dc measurements. However, despite such desire, no one in the past has developed a practical, cost-effective instrument that is capable of accurately measuring the characteristics of a sample using both ac and dc techniques.

The present applicants have developed a preferred embodiment magnetic measurement system that is versatile, highly accurate, and can measure both AC susceptibility and DC moment. The instrument provided in accordance with a presently preferred exemplary embodiment of the present invention includes various components (i.e., two oppositely wound secondary coils, a source of AC excitation current coupled to a primary winding, and a stepping motor for moving the sample between the coils) to perform AC susceptibility measurements. The instrument also includes a source of DC current that can be coupled to the primary winding. The motor and associated sampling positioning arrangement is also used to provide the motion needed for "extraction type" DC magnetization measurement. A high speed digital voltmeter monitors and records the output of the secondary coil(s). The recorded output of the digital voltmeter is numerically processed (using a computer) to yield the voltage integral indicative of magnetic moment.

Thus, a presently preferred exemplary embodiment of the present invention provides a combination of the extraction technique for DC moment measurement with the AC susceptibility measurement using a common sensing structure—all within an instrument providing state-of-the-art electronics and computer control. By way of non-limiting example, applicants' presently preferred embodiment system provides the following advantages:

A single instrument, requiring no hardware reconfiguration between measurement modes, that is capable of measuring both AC and DC magnetic response of materials;

AC and DC measurements can be made without removing sample from dewar—thereby eliminating possible errors due to changes in set-up, changes in sample condition, etc.;

Use of common components (e.g., coil assembly) permits common calibration factors to be used for both AC and DC measurements;

Calibration constants for both AC and DC measurements can be calculated from considerations of coil geometry alone (unnecessary to calibrate with standard magnetic materials—since the coil assembly is precision wound and the system has been designed to avoid extraneous effects);

Stepper motors and associated sample suspension/mounting structure used for DC magnetization extraction technique also used for moving sample during AC measurements in order to cancel out differences between the two coils;

Dual opposed secondary coils cancel magnetic field noise;

Non-zero voltage offsets within the digital voltmeter during DC measurements are cancelled during subsequent noise reduction analysis—permitting higher speed digital voltmeter data acquisition in order to minimize "dead time" between measurements and thereby increase measurement sensitivity;

AC susceptibility measurement sensitivities comparable to or greater than those achievable using SQUID magnetometers (e.g., $2 \times 10^{-8}$ emu);

High dc measurement sensitivity levels (e.g., $5 \times 10^{-5}$ emu) can be achieved with an effective dynamic range extending to $>10^3$ emu, comparable to Vibrating Sample Magnetometers;

Broad dynamic range ($10^{-8}$ to $>10^3$) to permit a wide array of material properties to be studied;

AC susceptibility measurement over a wide range of temperatures (e.g., <4.2K. to 325K.), amplitudes (e.g., 0.1 A $m^{-1}$ (0.00125 Oe) to 1600 $Am^{-1}$ (20 Oe) RMS), and frequencies (e.g., 1 Hz to 10 kHz);

DC moment measurement over a wide range of temperatures and DC fields (e.g., 1.0 tesla or 5.0 tesla, plus or minus);

Capability of measuring harmonic susceptibilities, and AC and DC resistance (e.g., Hall effect, Transport $J_c$, magnetoresistance);

For AC measurements, primary coil is driven with an AC current source so that the resultant AC field depends only on the "constancy" of the current source output—thereby eliminating complicated phase relationships dependent on measurement frequency or temperature;

Virtual elimination of effects of eddy current generation in conductive materials or generation of persistent currents in superconductive solenoids inductively coupled to the secondary coils;

Fully automated for unattended operation with data acquisition and control software that is quickly and easily tailored to address specific research requirements;

Possible to input sample parameters (e.g., volume, mass) and demagnetization factors to assure that the resultant measurement is as accurate as possible;

Wide range of materials and applications. The system is well suited for studying paramagnetic and ferromagnetic materials, amorphous alloys and diluted magnetic semiconductors, organic ferromagnets and organic superconductors ($C_{60}$ compounds), conductive polymers, thin film recording media, etc.

Ability to flexibly configure a common instrument platform for AC measuring capabilities, DC measuring capabilities, or both—without sacrificing accuracy of either measurement mode.

Expandable configuration to permit purchasers to upgrade measuring system by adding additional measurement mode capabilities subsequent to purchase.

Applicants have thus developed a single instrument that incorporates both a dc moment measurement scheme and an ac susceptometer. The instrument provides a sensitive dc measurement capability which can be simply implemented, without sacrificing any of the performance characteristics of the ac measurement.

After considering a number of standard dc moment measurement schemes, applicants chose an extraction technique. Extraction refers to many variations of a basic method, but generally involves moving (extracting) a magnetized sample from within a sensing coil. The voltage induced in the coil is detected and integrated over time to yield the total flux change in the coil. The flux change is directly related to the magnetic moment of the sample. An extraction method is attractive for this application since all required experimental hardware is already in place for the ac susceptibility measurement. The only missing component is the means to detect the voltage induced in the sensing coils. After reviewing experimental requirements and instrument specifications, applicants decided to use a high speed digital voltmeter (DVM). The DVM specifications indicated that performance comparable to, or better than, a commercial fluxmeter could be achieved.

One aspect of the present invention thus provides a relatively simple arrangement to provide adc moment measurement capability in an ac susceptometer requiring minimal effort and hardware changes. Performance is comparable to many systems constructed solely as adc magnetometer. An important element to the measurement in the preferred embodiment is the use of a high speed digital voltmeter (DVM) for the signal analysis. In addition to providing the required resolution and sensitivity needed for the moment measurement, the features of the DVM can be used to add further capabilities to the system at minimal expense. For example, with the addition of a sample probe, a dc resistance measurement can now be performed.

BRIEF DESCRIPTION OF THE DRAWINGS

These and other features and advantages of the present invention will be better and more completely understood by referring to the following detailed description of a presently preferred exemplary embodiment in conjunction with the drawings, of which.

DETAILED DESCRIPTION OF A PRESENTLY PREFERRED EXEMPLARY EMBODIMENT

Figure 1:
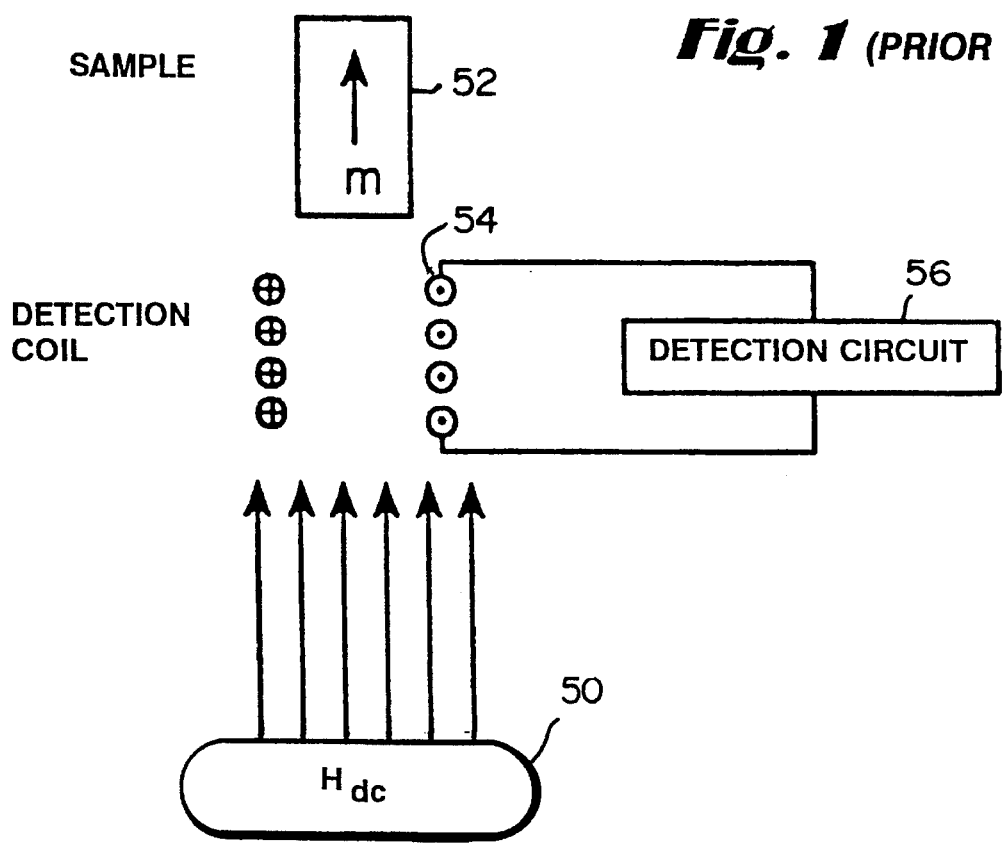
FIG. 1 is a schematic illustration of an exemplary prior art DC magnetometer.
Figure 2:
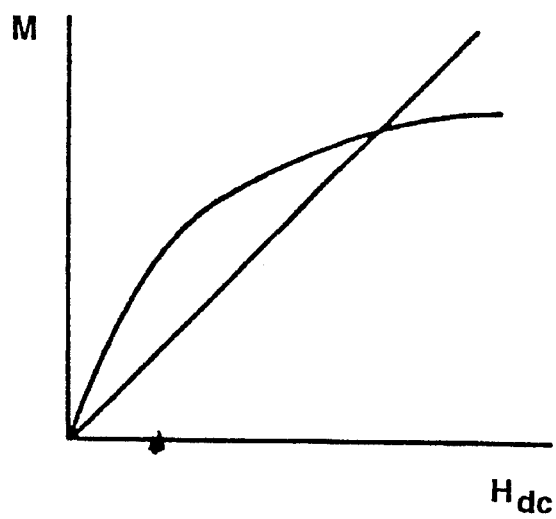
FIG. 2 is a graphical illustration of exemplary magnetization curves for two different samples.
Figure 2A:
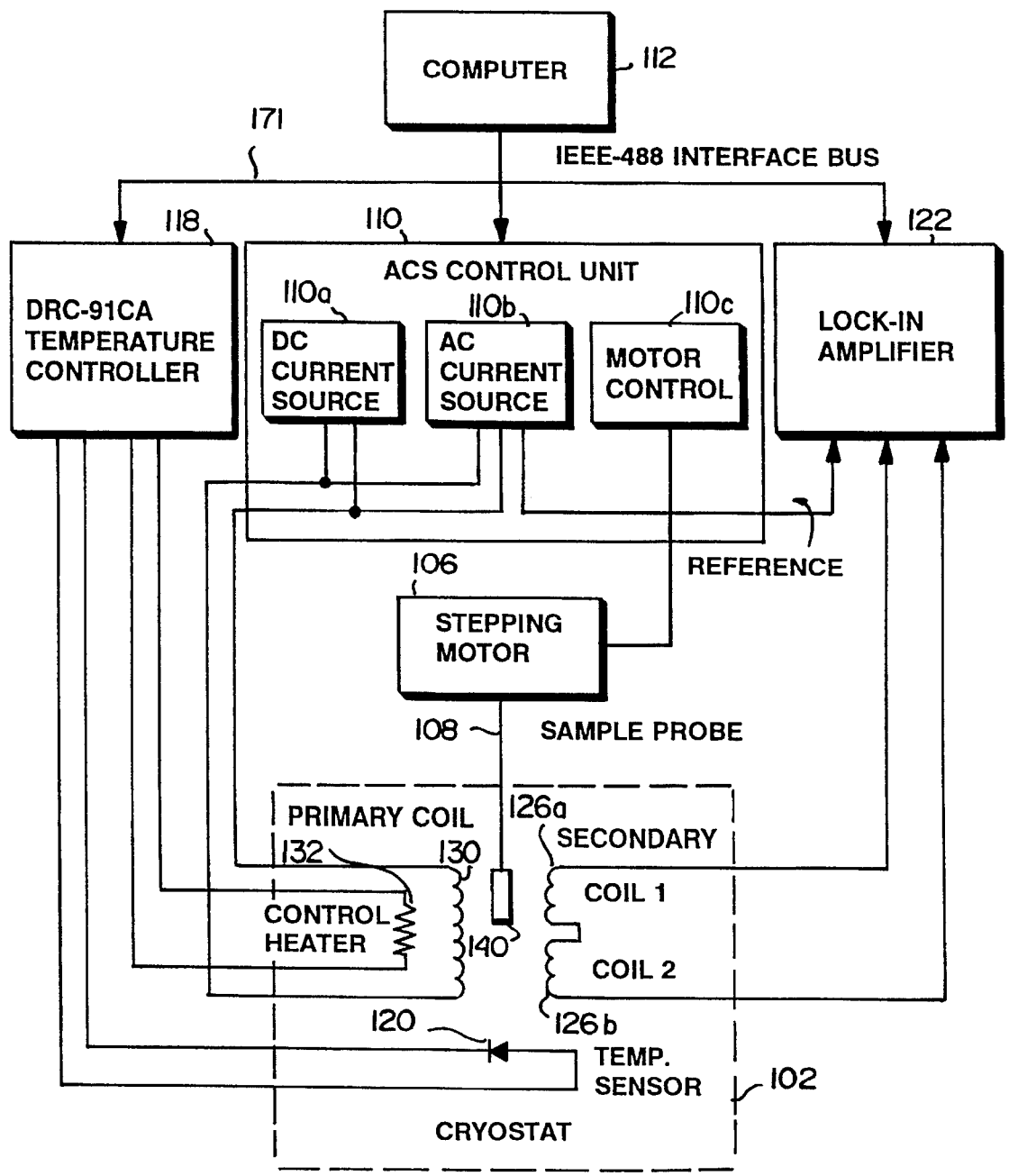
FIG. 2A is a schematic block diagram of an exemplary prior art ac susceptometer arrangement.
Figure 3:
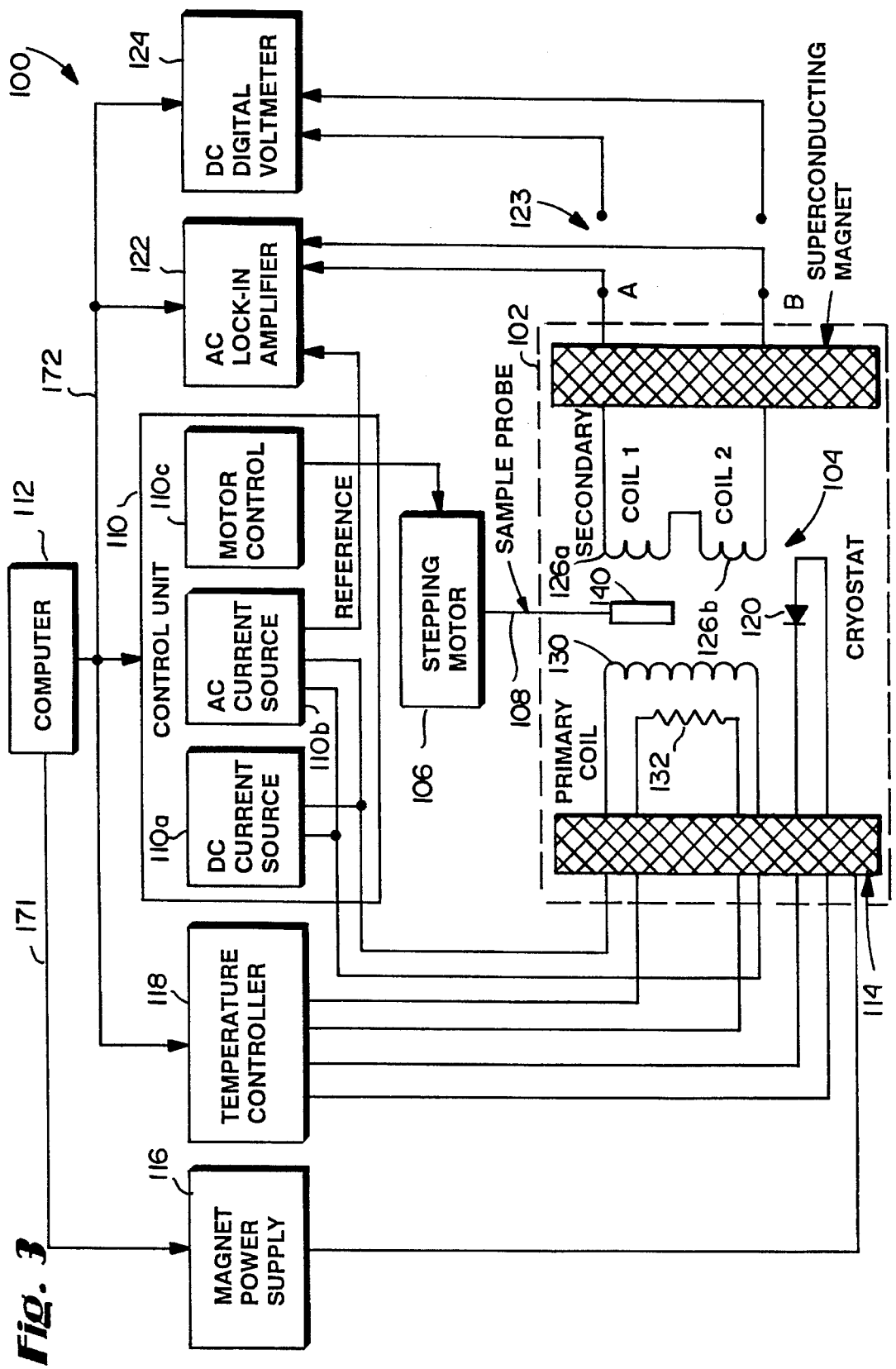
FIG. 3 is a schematic block diagram of a presently preferred exemplary embodiment of a magnetic measuring system in accordance with the present invention.

FIG. 3 is a block schematic diagram of a presently preferred exemplary embodiment of a magnetic measuring system 100 in accordance with the present invention. FIG. 3 uses common reference numerals to designate elements that are similar or identical to those shown in prior art FIG. 2A. However, the fact that common reference numerals are used between the two Figures does not necessarily mean that elements designated with common reference numerals are identical in all respects. For example, even though computer 112 appears in both prior art FIG. 2A and in FIG. 3, the FIG. 3 computer executes different software to provide additional/different functionality (e.g., capability to measure dc magnetization) such that it is not identical to the FIG. 2A computer.

Referring to FIG. 3, system 100 includes a cryostat 102 housing a coil assembly 104; a stepping motor 106 mechanically coupled to a sample probe 108; a control unit 110; a computer 112; a superconducting magnet 114 and associated magnet power supply 116; a temperature controller 118 and associated temperature probe 120; an AC lock-in amplifier 122; and a digital voltmeter (DVM) 124.

Figure 4:
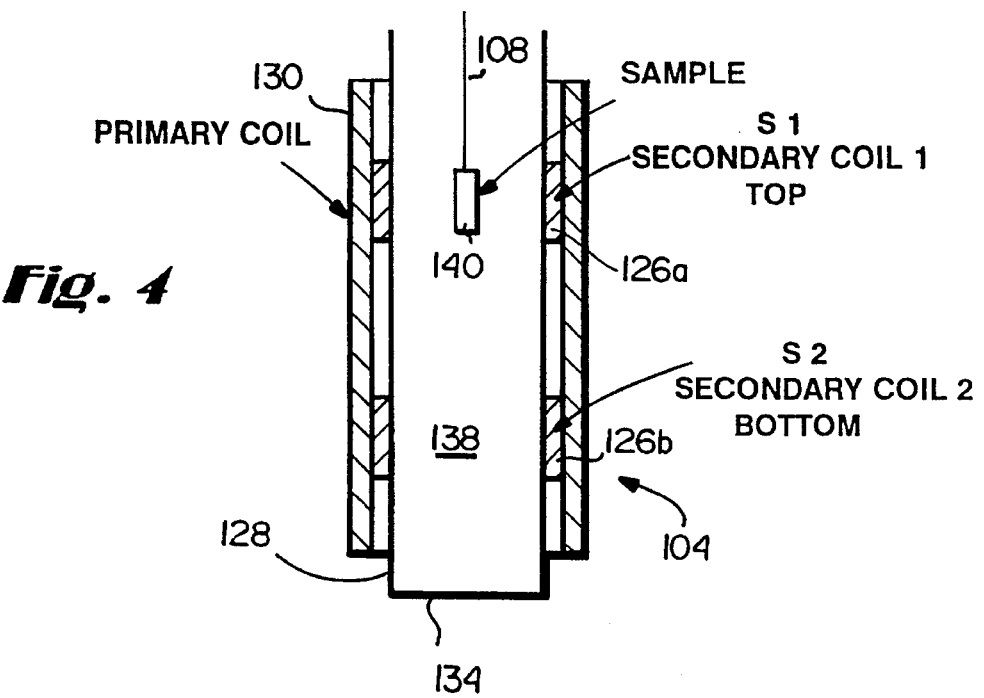
FIG. 4 is a schematic illustration of an exemplary sample coil arrangement shown in FIG. 3.

Referring now to FIG. 3 and to FIG. 4 (a simplified cutaway view of coil assembly 104), two sensing (secondary) coils 126a, 126b are identical but oppositely wound on a sapphire tube 128 in the preferred embodiment. Each coil 126a, 126b is perfectly wound and contains approximately 1600 turns with a mean diameter of 1.1 cm and a length of 1.9 cm in the preferred embodiment. Secondary coils 126a, 126b are positioned coaxially with a center-to-center distance of 3.8 cm in the preferred embodiment. A 1300 turn primary coil 130 is wound directly over the top of the two secondary coils 126a, 126b in the preferred embodiment. Thus, the three coils 126a, 126b and 130 are all coaxial with one another, with primary coil 130 being wound over and covering both of secondary coils 126a, 126b. As will be appreciated, the spacing between secondary coils 126a, 126b is such that when sample 140 is within the space defined within the interior of secondary coil 126a, it is outside of the interior space within (and is also magnetically isolated from) secondary coil 126b. However, so long as sample 140 is at least partially positioned within the interior space within any of secondary coils 126a, 126b, the sample is fully within the interior space within primary coil 130.

The primary coil 130 is used in the preferred embodiment to generate the ac field for ac susceptibility measurements, but it can also be used to generate low level dc fields for the extraction type DC magnetization measurement. The overall design of the coil assembly 104 in terms of its physical size and number of turns is critical for the ac measurement (as those skilled in the art will readily recognize), as it determines the frequency response and ac field range.

Temperature sensors 120 and control heaters 132 are also mounted with the coils 126, 130 on the outside of the sapphire tube 128. The entire coil assembly 104 is wrapped with coil foil and superinsulation and sealed at one (i.e., the lower) end 134 in the preferred embodiment. The sapphire tube 134 includes an open end 136 through which the sample probe may descend into an interior space 138 within the center of coil assembly 104. As will be explained in detail below, the sample probe 108 is positioned and moved by stepping motor 106 so as to precisely position and move a sample 140 within sample space 138 with respect to secondary coils 126a, 126b.

Figure 5:
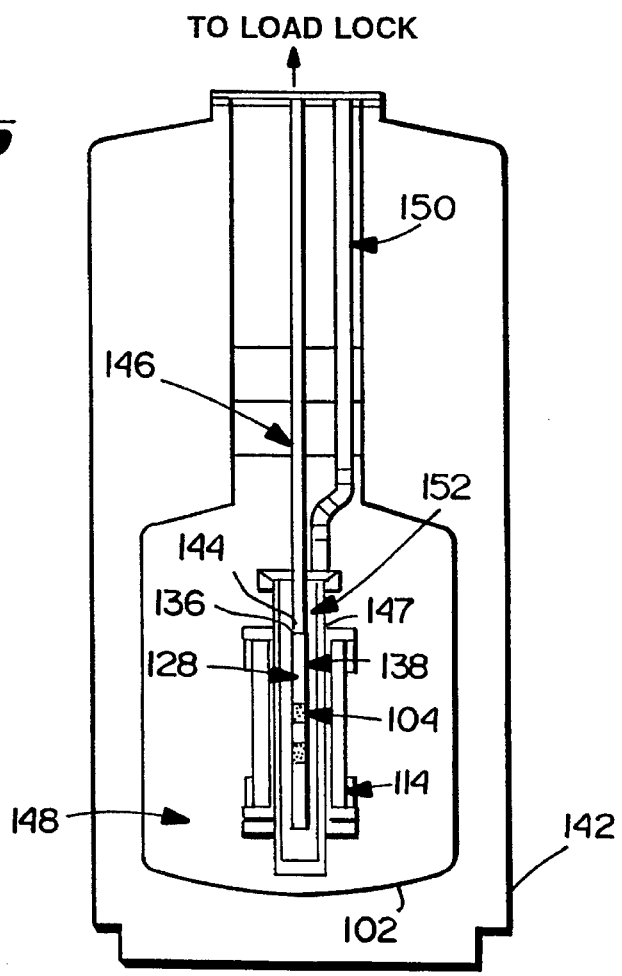
FIG. 5 is a schematic diagram of an exemplary cryostat as shown in FIG. 3 mounted within a helium dewar.

FIG. 5 is an exemplary cut-away view of cryostat 102 shown in FIG. 3 mounted within a helium dewar (refrigerator) 142. As shown in FIG. 5, the open end 136 of the sapphire tube 128 is attached to the lower end 144 of a stainless steel tube 146 inside a vacuum jacket 147. This permits sample space 138 to be isothermal and thermally isolated from the cryogenic (e.g., liquid helium) bath 148. The sample space 138 is normally operated with helium exchange gas inside to provide the necessary thermal coupling between the sample 140 and the thermometers 120. Controlled temperatures from below 4.2K to 330K can be achieved. A vacuum line/wire feed 150 is coupled to a vacuum isolation space 152 within vacuum jacket 147 to permit vacuum to be drawn from the isolation space and to provide a path for electrical conductors coupling external equipment to the superconducting magnet 114, the coil assembly 104, and the other electrical components within cryostat 102.

Figure 6:
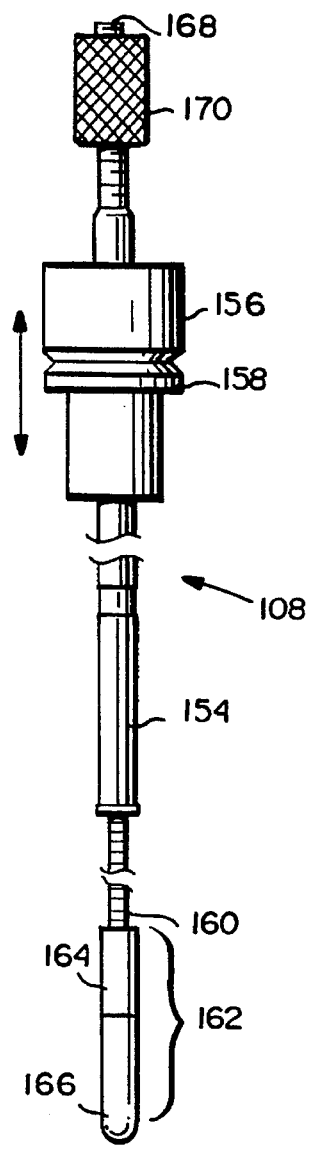
FIG. 6 is an elevated view of an exemplary sample mounting arrangement shown in FIG. 5.

FIG. 6 is an elevated side view of an exemplary preferred embodiment sample probe 108. Sample probe 108 descends, in the preferred embodiment, through stainless steel tube 146 into sample space 138. The preferred embodiment provides access to the secondary coils 126a, 126b and sample space 138 from above through a room temperature load seal assembly 156 and associated sample probe load seal (not shown) using a sample rod 154. Sample probe load seal assembly 156 in the preferred embodiment includes an O-ring seal 158 located on a lower portion thereof that makes a vacuum tight seal between the probe seal and the load seal. Side-mounted opposed thumb screws (not shown) in the load seal pull the probe seal 156 downward to compress the O-ring, and also hold the seal snugly in place to prevent any relative movement between the load seal and the probe seal during sample movement.

Sample rod 154 in the preferred embodiment is a 0.64 cm diameter polished stainless steel rod with a nylon extension 160 and sample mount 162. The sample rod 154 slides through vacuum-tight Teflon O-ring probe seal assembly 156, permitting the sample 140 (which is disposed within sample mount 162) to be moved up and down while maintaining a vacuum seal in the sample space 138. This arrangement allows samples 140 to be exchanged while the system is at cyrogenic temperatures. In the preferred embodiment, sample mount 162 includes a nylon (e.g., Delrin) bushing 164, a Delrin sample holder 166, and a holder lid (not shown, may comprise a #10–24 threaded Delrin rod for mechanically coupling bushing 164 to sample holder 166).

Once the sample 140 has been inserted into the sample probe 108 and the sample probe has been inserted into the sample space 138 within the secondary coils 126, an upper, threaded end 168 of the sample rod 154 is attached to stepping motor 106 via a finder nut 170. Stepping motor 106 positions and moves the sample 140 between the two secondary coils 126a, 126b under control of control unit 110. In the preferred embodiment, the ac measurement technique uses a two-position measurement scheme to eliminate uncertainties which arise from slight imbalances between the two secondary coils 126a, 126b. In the preferred embodiment, this same movement mechanism (i.e., stepping motor 106 and associated mechanical coupling) is used in the dc moment measurement.

Referring once again to FIGS. 3 and 5, a 7.6 cm diameter 1 tesla superconducting magnet 114 is mounted on the outside of the vacuum space 152 in direct contact with the liquid helium bath 148. In the preferred embodiment, the magnet 114 is designed to have a uniformity of better than ±0.1% over the full axial length of the secondary coils 126a, 126b. The large diameter is used to minimize inductive coupling to the primary and secondary coils 126, 130 which adversely affects the ac measurement. The magnet 114 is used in the preferred embodiment both for applying, to the sample, the magnetic field required for the dc moment measurement; and also for applying a dc bias field to the sample when making ac measurements. In order to vary fields easily and rapidly, a persistent switch is not used in the preferred embodiment.

Referring once again to FIG. 3, system 100 is designed for automatic operation and all control is done through computer 112. The sample movement, temperature control, field control, and data acquisition are all executed under software control by computer 112. Magnet power supply 116 selectively provides power to superconducting magnet 114 under control of computer 112 (e.g., via an RS-232 serial link 171). In the preferred embodiment, magnet power supply 116 comprises a convention Lake Shore Model 610 or 612 magnet power supply.

In addition, computer 112 is connected, in the preferred embodiment, via an IEEE 488 interface bus 172 to permit it to control the operations of temperature controller 118, control unit 110, AC lock-in amplifier 122, and DVM 124. In the preferred embodiment computer 112 comprises a general purpose off the shelf personal computer (e.g., the Hewlett-Packard VECTRA (TM) computer and associated monitor and keyboard) that includes an IEEE-488 (GPIB) board and internal hard disk (not shown). Software stored on the internal hard disk permits computer 112 to control the operations of system 100.

In the preferred embodiment, AC lock-in amplifier 122 comprises a commercially available EG&G Model 5209 Lock-in amplifier that is controlled by computer 112 via bus 172. Briefly, lock-in amplifier synchronizes with an AC reference (excitation) signal provided by control unit 110 in order to "lock in" to and amplify a version of the ac excitation signal received by secondary coils 126a, 126b. Lock-in amplifier 122 provides a highly accurate measurement of the parameters of the AC signal it is "locked in" to (synchronous detection being used to eliminate noise effects and to make the instrument phase sensitive so as to permit imaginary susceptibility components to be detected, as is well known).

Control unit 110 preferably comprises a Lake Shore model 140 or 710 ACS Control Unit that includes an internal DC current source 110a, AC current source 110b, and motor control 110c. In the preferred embodiment, the outputs of the AC and DC current sources 110a, 110b are coupled to primary coil 130, and these current sources are operable under direct, programmable control by computer 112. Thus, computer 112 may cause an adjustable amount of AC and/or DC current to primary coil 130 by controlling DC current source 110a and AC current source 110b via bus 172. In the preferred embodiment, AC current source 110b provides a reference current output that is applied to a "REF AC In" terminal of Lock-In Amplifier 122 (as described above).

Computer 112 also controls the operation of stepping motor 106 by writing appropriate information to control unit motor control block 110c. Stepper motor 106 in the preferred embodiment includes a movement motor head (not shown) providing a conventional stepping motor coupled to axially displace a threaded shaft, the threaded shaft being mechanically coupled to sample probe finger nut 170. The movement motor head preferably includes travel limit switches (not shown) of conventional design to limit the vertical travel of sample probe 108.

In the preferred embodiment, the secondary coils 126a, 126b are connected, in series, alternately and selectively to either lock-in detector amplifier 122 for the ac measurement; or to digital voltmeter 124 for dc measurement. Such alternate connections are accomplished in the preferred embodiment via connector network 123 (a switching network is avoided in the preferred embodiment in order to reduce noise; instead, the user manipulates cables to manually disconnect coils 126a, 126b to either the lock-in amplifier or to the digital voltmeter depending upon which measurement, ac or dc, is desired). In the preferred embodiment, DVM 124 comprises a modified Keithly Model 182 Sensitive Integrating Digital Voltmeter. This DVM 124 provides an output which is numerically processed by computer 112 to provide an integrated voltage value.

The Keithly Model 182 in unmodified form has excellent sensitivity, but does not sample rapidly enough to provide desired sensitivity in the preferred embodiment because it provides a substantial "dead time" between samples during which auto-zeroing compensation routines are performed (i.e., in order to compensate for non-zero voltage offsets generated within the meter itself so as to provide absolute voltage readings). The preferred embodiment employs a Keithley meter that has been modified to reduce "dead time" between samples by eliminating zero offset compensation functions (such that the DVM does not provide absolute voltage readings but instead provides only relative voltage readings). Thus, the preferred embodiment modified DVM 124 spends a higher percentage of the time making measurements (thereby increasing the amount of time during a given measuring sequence during which the output voltages provided by sensing coils 126a, 126b are being sensed). As a consequence of this modification, the modified DVM may, when connected to a zero input voltage, tend to drift between slight positive and slight negative voltage readings due to drifting within the input amplifiers and other associated stages of the meter itself. The preferred embodiment compensates for such meter offset voltage drifting - and at the same time compensates for background DC voltage picked up by secondary coils 126a, 126b - such that the absolute voltage readings of the Keithly DVM can be sacrificed for reduced "dead time" realizable by decreasing the amount of overhead processing performed in the "dead time" between successive samples. Although the modified meter drifts slightly over time, it provides sufficient stability over the time a measurement is actually being made so that errors in the relative voltage measurements it provides during a particularly magnetic characteristic measurement are relatively negligible. While not presently preferred due to its decreased sensitivity relative to the modified Keithley DVM, it is also possible to use a Hewlett Packard Model HP 3458A integrating DVM since it may give satisfactory performance and may have its own specific advantages depending upon what is desired from the measurement. In the preferred embodiment, "integrating" DVM 124 integrates the output of sensing coils 126a, 126b over relatively short time periods during measurement to provide many successive samples to computer 112. Computer 112 numerically processes these successive samples (as described below) to provide a value indicating dc moment.

Principles of Operation

A. DC Magnetization

Superconducting magnet 114 is activated during DC measurements in order to apply a constant, uniform magnetic field to sample 140. Primary coil 130 is typically deactivated during DC measurements, although it is sometimes desirable to apply a controlled amount of DC current to primary coil 130 in order to provide "fine" adjustment of the applied magnetic field. Thus, in the preferred embodiment magnet power supply 116 has an output that is adjustable in coarse increments; DC current source 110a permits "fine" magnetic field bias adjustments to permit the operator to, for example, measure more (or specific user-selected) points on the sample's magnetization curve.

The "extraction method" is used during the dc measurement - such that stepping motor 106 moves the sample from the axial center of secondary coil 126b to the axial center of secondary coil 126a (and, in the preferred embodiment, back to the axial center of secondary coil 126b) during the time DVM 124 is acquiring a measurement. Sample movement results in a change in magnetic flux that is detected by secondary coils 126a, 126b and induced voltage measured by DVM 124 to provide a measure of the net magnetic moment of the sample. Secondary coils 126a, 126b are wound identically (albeit in opposite directions) and are intended to have identical characteristics so that background voltage (e.g., due to stray magnetic fields) induced in one coil is cancelled by the same background voltage induced in the other coil.

In the extraction measurement, the voltage as a function of time induced in the secondary coil by the moving sample [υ(t)] is not as important as the determination of the integral of the voltage over time. This integral gives the total magnetic flux (Φ) change through the coil due to the sample movement:

$$\Phi = -\int \upsilon(t)dt. \tag{1}$$

Note that the flux change will be independent of how the movement is executed; the result only depends on the starting and stopping points of the sample 140. Variations in the mechanics of the movement may change the shape and appearance of υ(t), but not the value of the integral. The use of two oppositely wound secondary sensing coils 126a, 126b as in the preferred embodiment will double the integral in (1), but more importantly will minimize induced noise from the environment and the applied field.

The magnetic flux can be related to the magnetic moment (m) of the sample through a calibration coefficient, α:

$$m = \alpha \Phi . \qquad (2)$$

The calibration coefficient can be determined experimentally with known magnetic standard samples, or, if the coil and sample geometry are known, a value for α can be calculated.

As mentioned above, during the DC measurement the sample 140 is moved from the center of one of the secondary coils 126a, 126b to the center of the other secondary coil. Thus, the sample 140 remains within the region of the field uniformity created by superconducting magnet 114 and/or primary coil 130 at all times (since the secondary coils 126 each lie entirely within the interior space defined by superconducting magnet 114 in the preferred embodiment, and also each lie entirely within the interior space defined by primary coil 130). This movement also minimizes uncertainties related to sample positioning since the voltage induced by a sample at a coil center is effectively zero. Note this will not be generally true for every two-coil system but depends on the coil/sample geometry and the flux coupling between the sample and each of the two secondary coils 126a, 126b.

Initially, it is necessary to position the sample 140 to be in the center of one or the other of secondary coils 126a, 126b - and for the operator to inform computer 112 which secondary coil the sample is positioned within. To initially position the sample 140 prior to a DC measurement, the operator sets a DC field and selects a "position" routine in the control software. The operator then uses his or her "best guess" to select which secondary coil 126 (upper or lower) the sample is believed to be within. A test scan is then performed to automatically move the sample by a displacement corresponding to the distance between secondary coils 126a, 126b. This will yield voltage peak outputs of the type shown in FIG. 8. For a properly positioned sample, the voltage peaks will be perfectly symmetrical. for in incorrectly positioned sample, on the other hand, non-symmetrical peaks will result. In the preferred embodiment, an improperly positioned sample 140 should be repositioned by moving the sample up or down as needed. This process is repeated until a symmetrical voltage peak curve is obtained.

This positioning technique may be difficult to perform for samples with very low signals. When the baseline "scatter" is comparable to the signal due to small sample size, it may be possible to increase the field strength in order to increase signal level. As a least resort, manual positioning of sample rod 154 (e.g., through a process of physically measuring the length of the sample, relative to the distance between secondary coils 126a, 126b, and marking the rod accordingly) may be used to properly position the sample.

In order to obtain a measurable voltage signal (i.e., a voltage signal of a sufficiently high level to be measurable), a rapid sample movement is required. However, there is a limit as to how fast the stepping motor 106 can move the sample rod 154 through the relativeiy tight o-ring seal 156. Changing to a different movement mechanism was considered, but the benefits of a stepping motor 106 outweighed the constraints it placed on the measurement. A sample velocity of several cm/sec was determined sufficient to meet the desired moment specifications. Except as noted, all measurements were performed with a sample velocity of 2.4 cm/sec.

Figure 7:
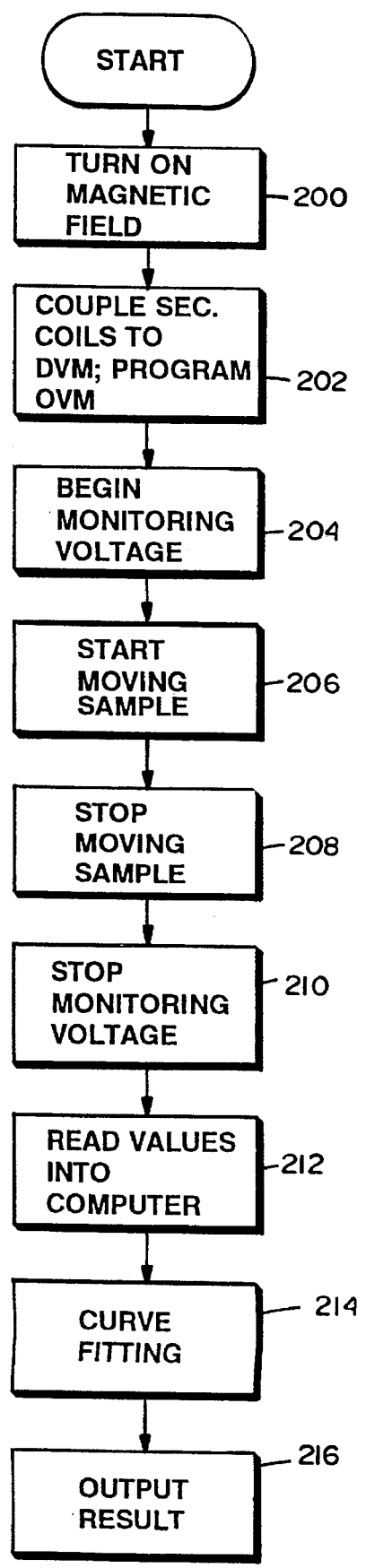
FIG. 7 is a flowchart of exemplary program control steps performed by the preferred embodiment computer to provide a dc magnetization measurement.
Figure 9:
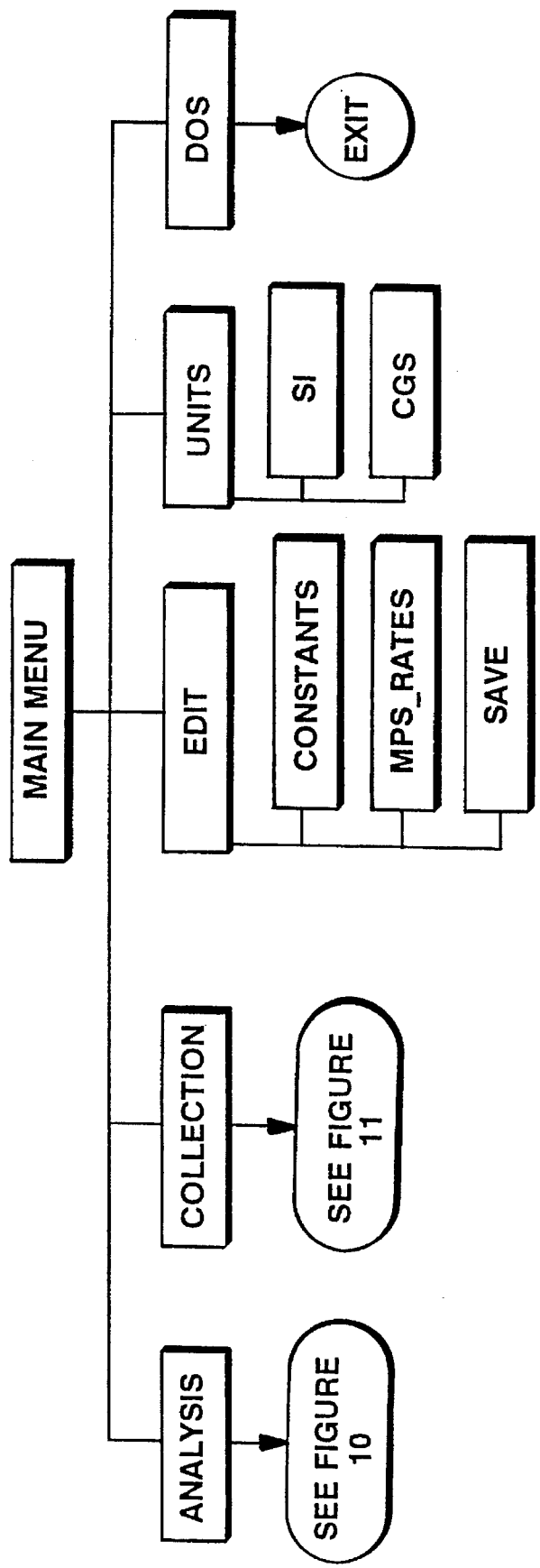
FIGS. 9–12 are schematic diagrams of exemplary menu option breakdowns suitable for providing dc measurement capabilities in the FIG. 3 embodiment.
Figure 10:
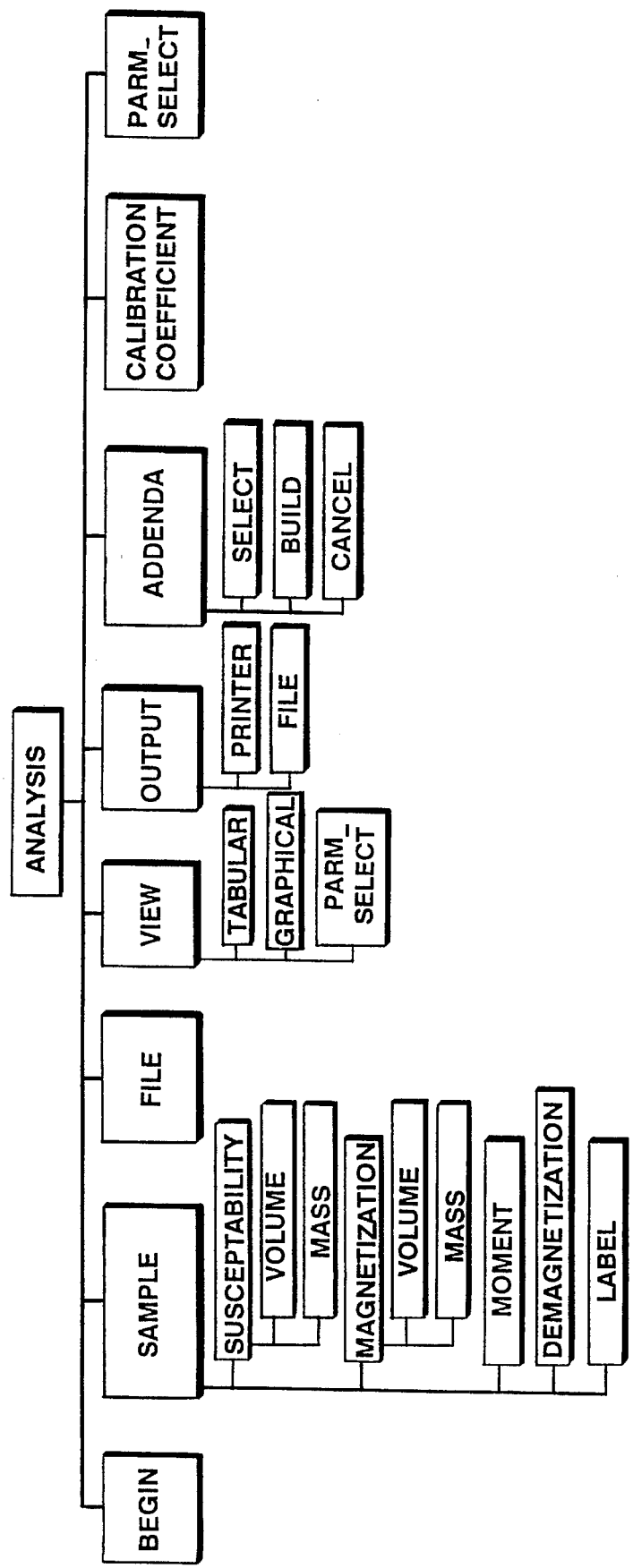
Figure 11:
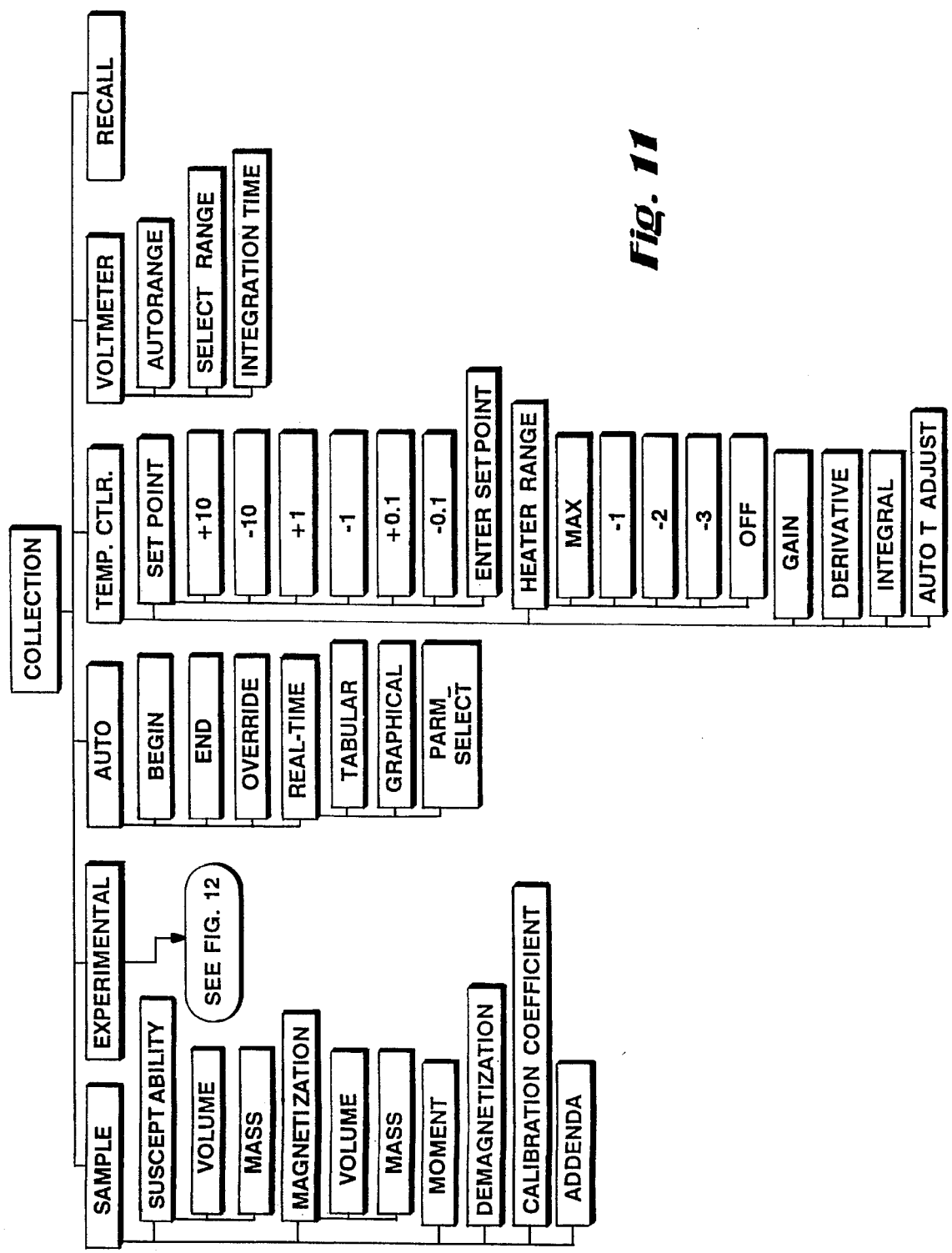
Figure 12:
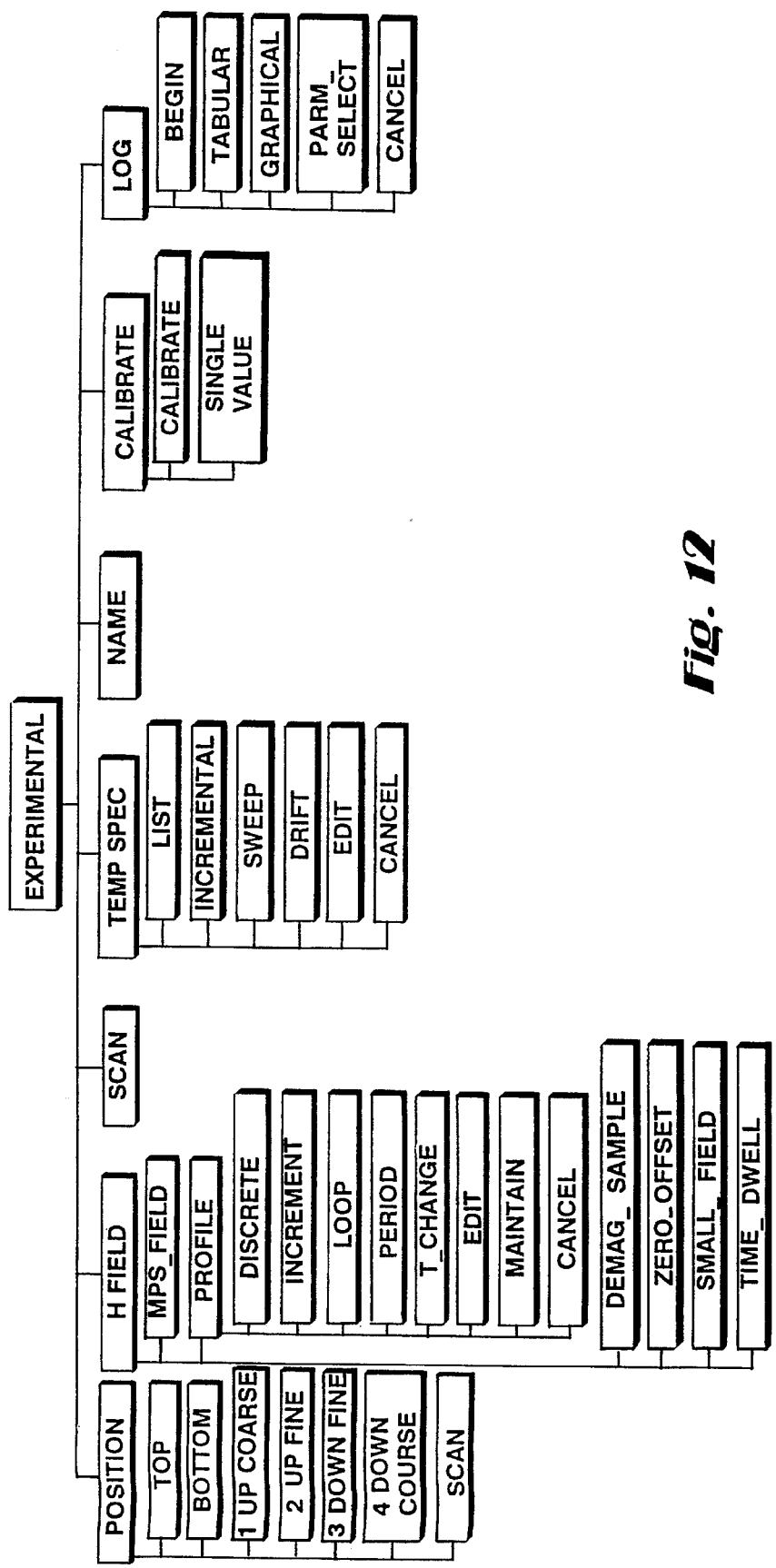

FIG. 7 is a high level flowchart of measuring steps performed by system 100 to provide a DC magnetization measurement. Initially, computer 112 controls magnetic power supply 116 (and possibly also DC current source 110a) to provide generate a constant magnetic field of specified intensity (block 200). Secondary coils are coupled to DVM 124 (via connection network 123), and the DVM is programmed to integrate with desired sampling times and for a desired overall integration time (block 202). The voltage induced in the secondary coils 126a, 126b is logged with high speed integrating voltmeter 124. Voltmeter 124 allows computer 112 to specify the time period through which the voltmeter integrates the signal (τ) and the time interval between the start of each measurement (Δt). Note, by necessity, Δt>τ with the difference representing the integral processing time required for the DVM instrument 124 to complete a single measurement. For best noise rejection, τ is set at an integral multiple of the power line cycle (PLC). For the maximum reading rate, τ is set to the minimum permitted by DVM 124. All filtering, autoranging, and other features (e.g., auto zeroing) which may slow the reading rate are disabled.

In the preferred embodiment, computer 112 controls DVM to begin monitoring voltage prior to controlling stepping motor to begin moving the sample 140 (blocks 204, 206). In a single "scan" the sample is typically moved from the center of bottom coil 126b to the center of top coil 126a and then back to the center of bottom coil 126b. During a sample movement in the preferred embodiment, a series of approximately one hundred readings characterizing υ(t) are recorded and stored to the internal memory of DVM 124. Computer 112 then controls stepping motor 106 to cease moving the sample 140 (block 208), and finally, controls DVM to cease monitoring voltage (block 210). The voltage readings are then read back into the computer 112 (block 212) for processing.

The "scan" of blocks 204–212 may be repeated several (e.g., up to 10) times to provide a single averaged value (e.g., for measuring samples with low level signals or when extra precision is required). The preferred embodiment system 100 permits a "half scan" mode (e.g., each movement of the sample 140, either up or down, defines one moment measurement). Such "half scans" are useful when rapid data acquisition is required (e.g., during a rapid field sweep). Since the accuracy and repeatability of the measurement is degraded somewhat when "half scan" is used, however, this mode is recommended for large samples or when noncritical measurements are being made.

Figure 8:
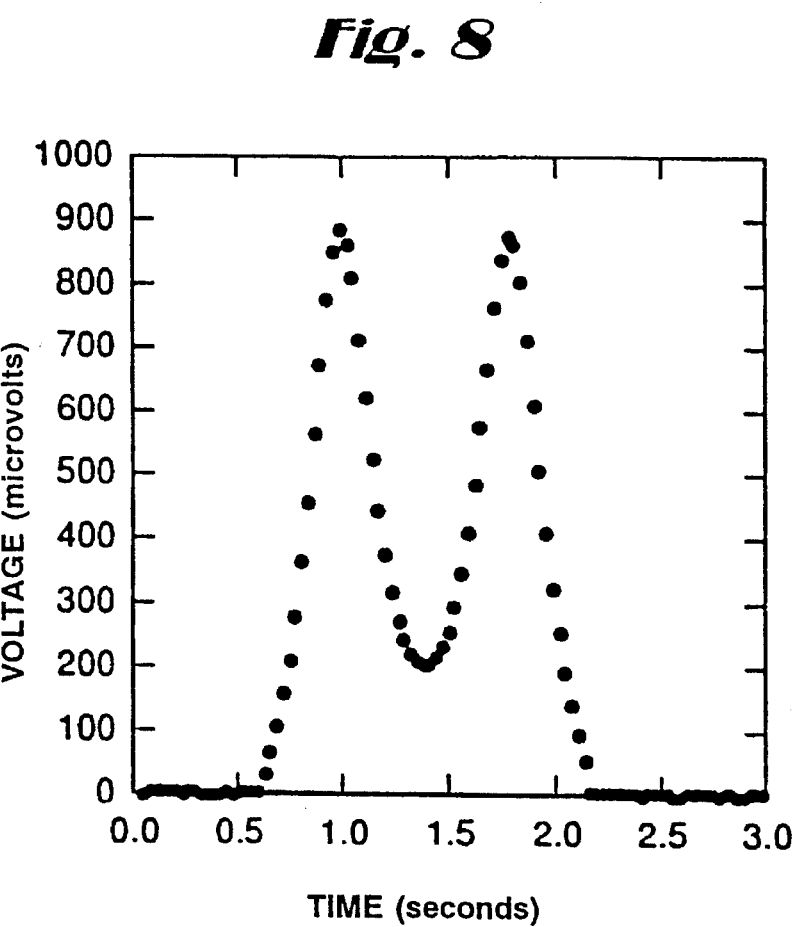
FIG. 8 is an exemplary graphical illustration of a voltage pulse recorded as the sample is moved from one secondary coil to another in the FIG. 3 embodiment.

The first step of the processing by computer 112 involves the elimination of uncertainties related t thermal emf's. The thermal emf's and any zero offsets are easily removed by monitoring the voltage in the sensing coils for a short period of time both before the movement starts (the time between performing blocks 204 and 206 shown in FIG. 7 is timed in the preferred embodiment) and after the movement stops (the time between performing blocks 208 and 210 of FIG. 7 is thus also timed by computer 112 in the preferred embodiment). The readings are linearly fit with respect to time in the preferred embodiment (FIG. 7 block 214) to create a baseline voltage which is subtracted from the measured voltages. This yields the true voltage data due to only the sample movement. Typical results are shown in FIG. 8. The voltage referred to in the description below is the voltage after correction for thermal emf's.

Each voltage measurement made by the DVM($v_i$) is actually a mean integral value over the integration period:

$$V_i = (1/\tau) \int_{t_i}^{t_i+\tau} V(t)dt \quad (3)$$

where $t_i$ denotes the start of the measurement process. What is required from (1) is the voltage integral over the complete pulse consisting of n voltage readings. This can be determined as follows:

$$\begin{aligned}\int_{t_i}^{t_m+\Delta t} V(t)dt &= \sum_{i=1}^{n} \int_{t_i}^{t_i+\Delta t} V(t)dt \\ &= \sum_{i=1}^{n} \left[ \int_{t_i}^{t_i+\tau} V(t)dt + \int_{t_i+\tau}^{t_i+\Delta t} V(t)dt \right] \\ &= \sum_{i=1}^{n} [V_i\tau + \epsilon_i]\end{aligned} \quad (4)$$

The second term in the summation, $\epsilon_i$, contains the contribution to the integral corresponding to the period $\Delta t-\tau$ the DVM is not integrating the voltage. If this time period is short, $\epsilon_i$, can be evaluated by approximating the voltage V(t) as the means value of the two voltage readings which span the time period.

$$\epsilon_i = [(V_i+V_{i+1})/2](\Delta t-\tau) \quad (5)$$

Substituting into (4), rearranging, and taking note of the fact that the initial and final voltage readings are zero yields the final result:

$$\int V(t)dt = \Sigma V_i \Delta t \quad (6)$$

This final expression appears exactly like a numerical integration using a trapezoidal approximation. However, what is physically occurring is not a numerical integration. This is a subtle but important distinction to understand. Since each reading of DVM 124 is actually proportional to the voltage integral over the time period $\tau$, the analysis using (6) will yield better results than what a strict numerical integration would imply. In a numerical integration, the error is a function of the data point spacing and curvature. The numerical error in (6) is due to the voltage approximation made in (5) and the magnitude of $\Delta t-\tau$, but not necessarily the number of data points.

The numerical error is important to understand because it affects both the absolute accuracy of the measurement and the repeatability from one movement to the next. If the voltage measurements were perfectly synchronized with the sample movement, each $v_i$ would always occur at exactly the same point in the voltage pulse. The evaluation of (6) would always give exactly the same numerical result but would be in error by the approximations made in (5). However, perfect synchronization would require timing to the millisecond level between the mechanical and electronic components. The effort to guarantee this is not justified, so in practice the $v_i$ fall at different points along the pulse for each sample movement. Slightly different numerical errors then arise in the evaluation of (6) which creates a non-repeatability associated with the numerical processing.

The time required to complete a moment measurement is dependent on how the measurement sequence is defined. A single scan measurement requires about 15 seconds to execute. Multiple scans may increase the measurement time (e.g., up to 150 seconds if 10 scans is selected). Computer 112 generates a moment value at the conclusion of the moment measurement sequence (block 216 FIG. 7).

The experimental feasibility of this approach and analysis was initially tested with the HP 3458A set to a 1 PLC (16.666 msec) integration time as DVM 124. The time between measurements could be set to as low as 16.69 msec, yielding an active DVM integration time over the total pulse of 99.86%. A permanent magnet sample was used to supply an output signal well above the noise floor of the voltmeter and the sample was moved at 1 cm/sec. The voltage integral was approximately 0.0104 volt-sec. Repeated movements of the sample showed a standard deviation of less than 25 ppm in the measurement and evaluation of (6). Also, as predicted in (5), with $\Delta t$ set to 20 msec, the standard deviation for repeated measurements increased to 150 ppm.

The effect of varying the integration time on the DVM was also tested using this same experimental set-up. The integration time was varied from 1PLC to 40 PLC while the time between readings was fixed at 0.023 milliseconds greater than the integration time. The results, consistent within ±20 ppm, verified the predicted independence on the number of voltage readings. Over two hundred points were recorded at 1 PLC while only 5 or 6 were recorded at 40 PLC. In all situations encountered to date, evaluating the integral by summing over a large number of readings yields the same or slightly better repeatability than using longer integration times with a fewer number of voltage readings. For this reason, a 1 PLC integration time has been adopted in the preferred embodiment.

The voltage noise floor and sensitivity limit can be determined by making repeated measurements with no sample present and comparing the standard deviation in the integral evaluations. Ideally, the results should be zero. The HP 3458A yields a lower limit of $\pm 2.5\times 10^{-7}$ volt-seconds in the evaluation of the integral. This corresponds to a moment sensitivity of approximately $\pm 10^{-3}$ emu ($10^{-6}$ Am$^2$). In the discussion of the preceding paragraphs, the standard deviation of 25 ppm reflects this noise floor and is not necessarily the limit to the reproducibility which might be achieved for large samples.

Most demands are for higher sensitivity as opposed to high resolution. For this reason, the final system configuration (as mentioned above) actually uses a modified Keithley 182 Sensitive Voltmeter instead of the HP 3458A. The Keithley instrument offers approximately a factor of ten improvement in voltage sensitivity and resolution, yielding a lower limit of $\pm 2.5\times 10^{-8}$ volt-seconds in the integral evaluation. This equates to about $\pm 10^4$ emu ($10^{-7}$ Am$^2$) in moment sensitivity. Voltages from the sensing coils of less than a microvolt can be readily detected and measured.

The increased sensitivity of the Keithley is at the expense of some speed and versatility. With the Keithley, voltage readings are limited to approximately 30 millisecond intervals. At 1 PLC integration times, the voltage is only integrated over 55% of the total time. Numerical errors associated with the approximation in (5) then limit the accuracy and repeatability of the integral determination to about ±0.1%. However, this is more than sufficient for most applications.

It will be understood that in some applications it may be desirable to change the magnetic field intensity between (or during) dc moment measurements. For example, it may be desirable to provide a magnetic field table to permit system 100 to automatically step through a series of predefined magnetic fields (so as to measure moment at various points along the magnetization curve of the sample). The preferred embodiment typically provides "wait"periods between field changes to permit the field to stabilize prior to making the next successive measurement, and also preferably directly monitors the current output of magnet power supply 116 to ensure accuracy. It is also possible to control magnet power supply to "ramp" at a user defined rate in order to "sweep" the magnetic field during a measurement (this may be useful to generate hysteresis curves for example).

CALIBRATION

In order to complete the moment measurement, the value of the calibration coefficient in equation (2) must be determined. The value of $\alpha$ is a measure of the flux coupling between the sample and the secondary coils and will vary with the sample size and geometry. A proper calibration therefore requires a separate calibration coefficient for each sample geometry measured.

However, samples are often small with respect to the sensing coils 126a, 126b and in these situations they can be approximated by magnetic dipoles. With this assumption and the simple secondary coil 126 geometry employed in this system, an expression for $\alpha$ can easily be derived in closed form. The calculations are similar to those used to derive an ac calibration coefficient. A magnetic dipole is assumed centered in one of the secondary coils and the field is integrated over the geometry of both the secondary coils 126a, 126b to give the total magnetic flux. The flux contained in the empty coil represents only 0.6% of this total, indicating that the two secondary coils 126a, 126b are nearly independent of each other. The total flux change when the sample is moved to the second coil is twice the calculated value. This gives a value for $\alpha$ of approximately 5300 emu/volt-sec (5.3 $Am^2$/volt-sec).

Larger samples with simple geometries, such as cylinders, can also be handled numerically. These types of calculations indicate that the dipole approximation is actually a very good approximation for most applications. For the present coil geometry and for samples up to 5 mm diameter and less than 10 mm long, the potential error due to the dipole approximation is less than 3%.

Since numerical values for $\alpha$ can be effectively calculated, the measurements made with preferred embodiment system 100 are absolute determinations of the moment. The accuracy is limited by the accuracy of the calibration coefficient which is estimated at 1 to 2 percent. The dimensions of the coil arrangement 104 are known to better than 1% and the effects of thermal expansion and contraction are only a few tenths of a percent. The two sensing coils 126a, 126b are matched to within 0.2% in the preferred embodiment as determined from their ac response or by measuring the induced voltage as the magnetic field is ramped. This level of calibration accuracy is comparable to what is often accomplished with standard samples.

For completeness, the calculated value for the calibration coefficient has been confirmed experimentally using NIST standard Ni and $MnF_2$ samples. The agreement is within the experimental uncertainty.

In a properly designed system which avoids eddy currents and other ac specific problems, the ac calibration follows directly from the dc calibration and vice versa. Both calibration coefficients relate the flux coupling between the coils and the sample. In the preferred embodiment, the DC calibration coefficient used is equal to $\pi$ times the ac calibration coefficient. Thus, a single calibration coefficient and associated analysis can be used for both ac and dc measurements. This has been tested experimentally by verifying that ac measurements are consistent with dc measurements for samples which show no ac related effects.

Preferred embodiment system 100 also provides a capability to measure the background signal attributable to the sample mount 162, sample rod 154, and anything else that may generate a background signal (e.g., substrate material etc.) during a moment measurement. The capability for subtracting the background signal form the data being recorded with the sample present is provided by software executing on computer 112. Such "addenda data" should be recorded using fixed temperature points over an applicable temperature range, and at least two applied fields which span the intended range of use (where one field can be zero field). A special option in the calibration analysis provided by the preferred embodiment processes the "addenda" data and stored the temperature/field/moment data to a file for later use. System 100 will automatically subtract the addenda data from a measured sample moments upon demand. The operator need only check the temperature T and field H at which the sample data was recorded. System 100 then uses the temperature/field/moment data in the addenda file to determine the addenda moment at temperature T and field H (i.e., a simple two-dimensional linear interpolation is performed); and subtracts the addenda moment from the actual sample moment.

FIGS. 9–12 show exemplary software menu structures provided by software executing on computer 112 to permit preferred embodiment system 100 to make dc magnetization measurements. Appendix A provides a listing of menu breakdown and functional description of FIGS. 9–12.

EXPERIMENTAL RESULTS

The dc moment measurement is made by making one complete movement cycle in the preferred embodiment; the sample is moved from the bottom to the top coil and the returned to the bottom. Two voltage integral evaluations are made and averaged to give the final moment output for the sample. This process requires approximately 15 seconds to complete. Averaging over multiple measurements improves the sensitivity and noise with a lower limit of $<5 \times 10^{-5}$ emu ($5 \times 10^{-8}$ $Am^2$). With the voltage ranges available in the DVM, there is no practical upper limit to the measured moment.

Figure 13:
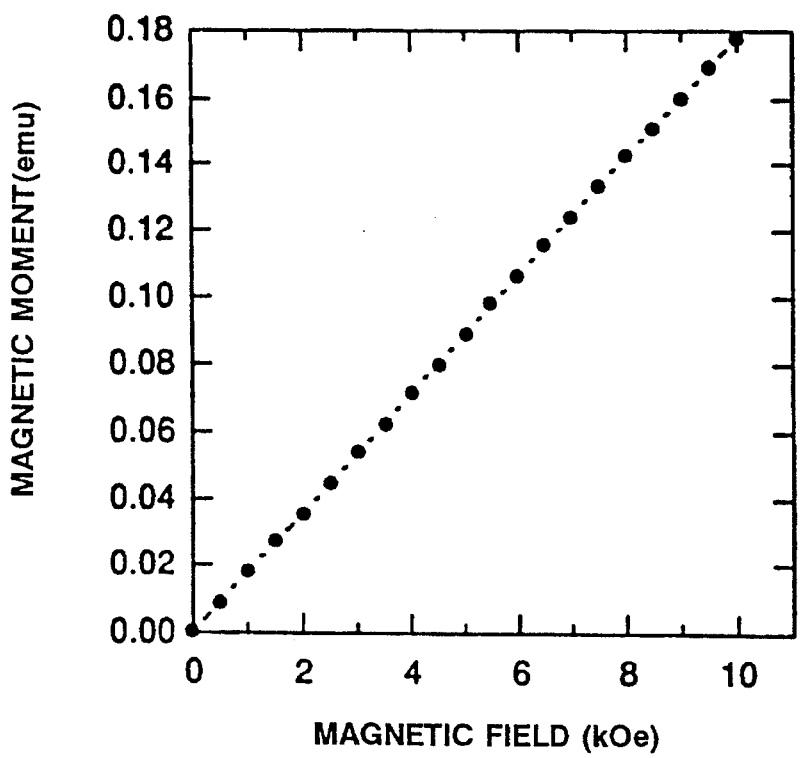
FIGS. 13 and 14 are, respectively, a plot of moment as a function of applied field for a NIST $MnF_2$ standard sample, and a plot showing deviation of such data from a linear fit, each of these plots being generated by the presently preferred exemplary embodiment of the present invention.
Figure 14:
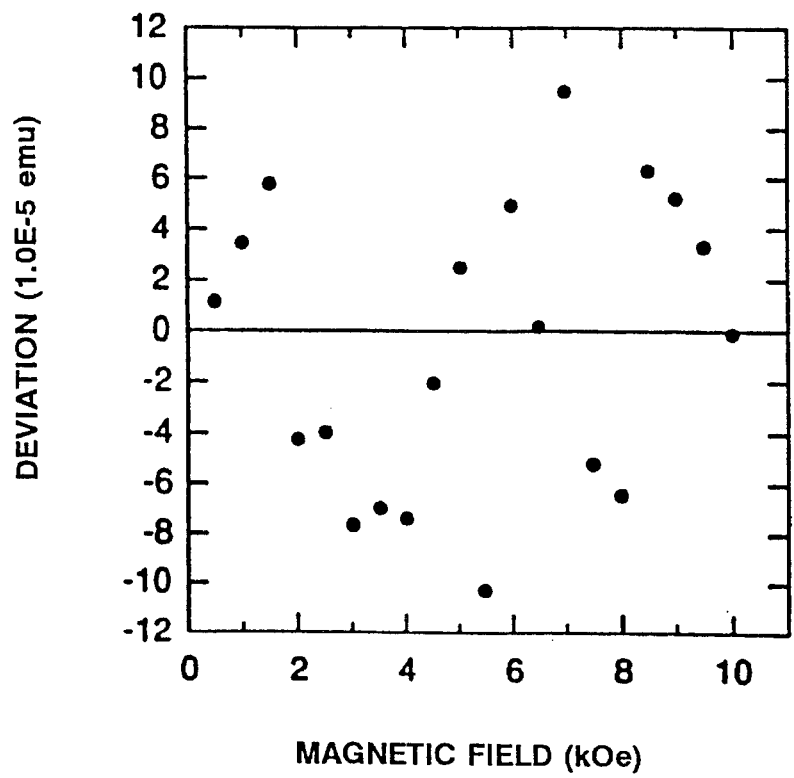

FIGS. 13 and 14 illustrate with a NIST $MnF_2$ standard sample what level of performance can be achieved. FIG. 13 shows the measured moment versus the applied field. The data should be linear over the range of fields used, and FIG. 14 shows the data plotted as a deviation from a straight line fit. The standard deviation about the line is $6 \times 10^{-5}$ emu - illustrating the excellent linearity in the measurement.

Repeated measurements over the course of an hour on a sample at fixed field gives reproducibilities of better than ±0.1%. When all experimental aspects are considered, including data processing, sample positioning, field setting, etc., the overall measurement reproducibility is a few tenths of a percent.

Image effects have been reported in superconducting magnets, and measurements were made to see if these effects could be detected. No effect was observed (<0.1%) which is probably due to the relatively large bore of the magnet 114 with respect to the sensing coils 126a, 126b.

Figure 15:
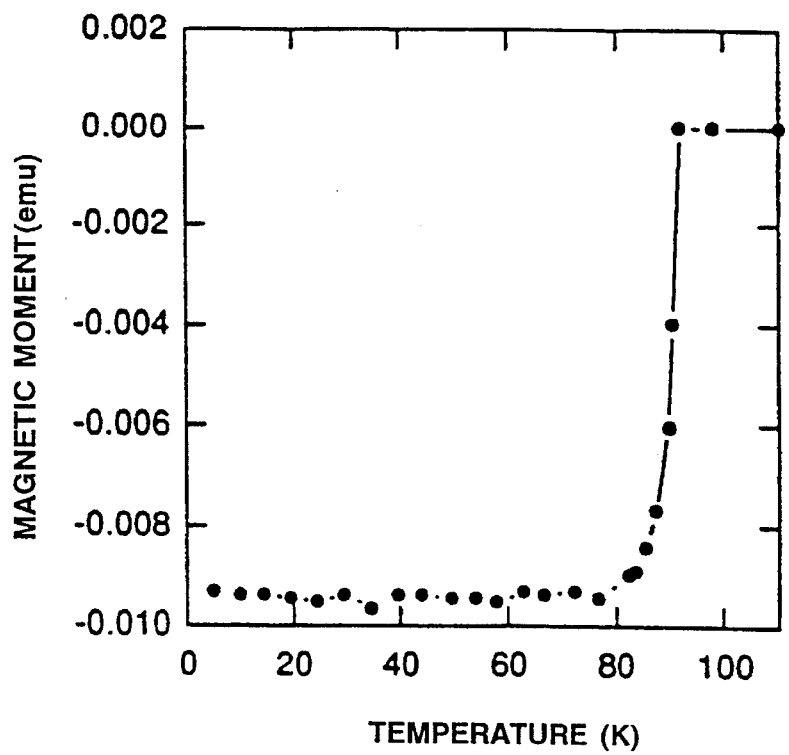
FIG. 15 is a plot of actual experimental results showing moment as a function of temperature for an exemplary single crystal YBCO sample at an applied field of 10 Oe.
Figure 16:
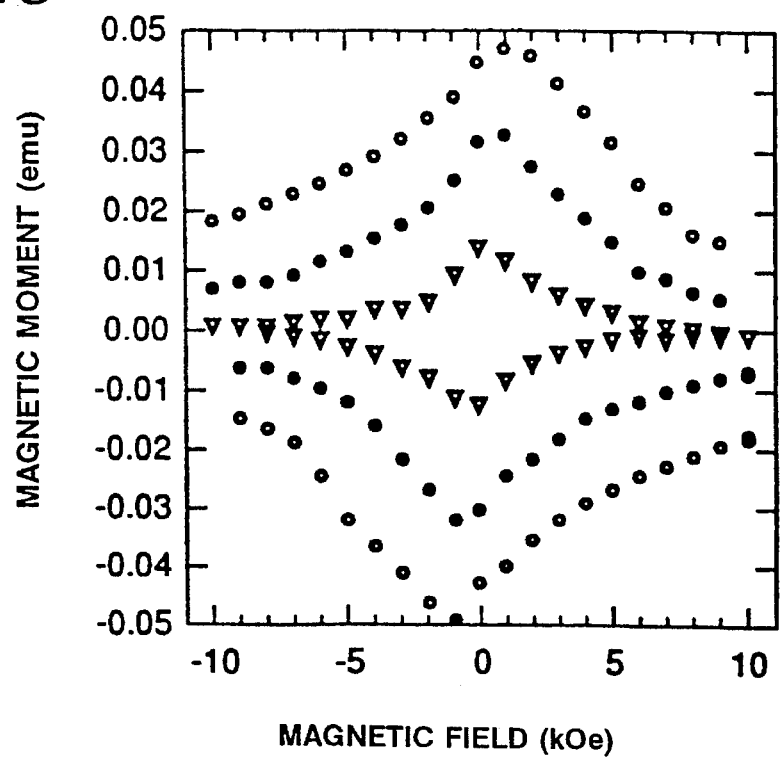
FIG. 16 is a plot of exemplary hysteresis curve experimental results for a thin film YBCO sample at 4.2K (open circles), 25K (solid circles), and 50K (triangles) collected during a single run of the preferred embodiment under automatic operation.

FIGS. 15 and 16 show typical dc moment results to further illustrate the capability and flexibility of the system. FIG. 15 shows moment as a function of temperature for a single crystal YBCO sample at an applied field of 100$e$ (the sample was zero field cooled and had a mass of 15.2 mg). FIG. 16 shows experimentally measured hysteresis curves for a thin film YBCO sample at 4.2K (open circles), 25K (solid circles), and 50K (triangles). Note the low dc field used in the data of FIG. 15 and the smoothness of the hysteresis loops of FIG. 16 for the samples with relatively low moments.

B. AC SUSCEPTIBILITY

System 100 performs ac susceptibility measurements in a manner that is substantially identical in principle to the ac measurement techniques used since 1988 in conjunction with Lake Shore's Model 7000 AC Susceptometer product (FIG. 2A is a block diagram of this prior art ac susceptometer arrangement showing similar or identical components to those used in the FIG. 3 preferred embodiment of the present invention).

Briefly, to perform an AC susceptibility measurement using the FIG. 3 preferred embodiment, the sample 140 is placed within sample space 140 and AC current source 110b is activated to provide a desired AC field to the sample via primary coil 130. Since the applied AC field is changing, the magnetization of the sample 140 changes in response. Secondary coils 126a, 126b measure changes in the magnetic field due to the susceptibility of sample 140 (the magnetization of which "follows" changes in the applied field may lag behind in an amount dependent on the magnetic response of the sample).

Superconducting magnet 114 does not need to be activated for AC susceptibility measurement. This is because most ac susceptibility measurements are desirably performed under low field conditions (although the superconducting magnet may be activated if high field ac measurements are desired, such as for "irreversibility line" type measurements). In addition, sample 140 is stationary during the time ac susceptibility parameters are being measured by lock-in amplifier 122.

In the preferred embodiment, stepping motor 106 is used to position sample 140 within the interior space of first one secondary coil 126b (at which time a first measurement is taken with sample 140 remaining stationary during the measurement); and is then used to position the sample within the interior space of the other secondary coil 126a (at which time a second measurement is made with the sample again remaining stationary during the second measurement). The two measurements are used by computer 112 to ascertain the magnitude and direction of the error between the two coils (such that the error can be cancelled out from one of the two measurements in Order to yield a highly accurate result). Hence, stepping motor 106 is used in the preferred embodiment during the ac susceptibility measurement process even though sample 140 is stationary during the time lock-in amplifier 122 is actually acquiring an ac measurement.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

APPENDIX A

5.3.2 MENU BREAKDOWN AND FUNCTIONAL DESCRIPTION

The following is a text-based representation of the information presented in the menu block diagrams.

Analysis
Display the Analysis menu
Begin
Processed data sent to printer or file depending on options selected in Output
Sample
Input sample specifications
Susceptibility
Select volume or mass susceptibility and input sample volume or mass
Magnetization
Select volume or mass magnetization and input sample volume or mass
Moment
Select moment (default selection)
Demagnetization
Enter demagnetization factor (and sample density if processing in terms of mass susceptibility or magnetization)
Label
Input sample label to be printed on printout
File
Input data file for processing
View
Display processed data on screen
Tabular
Displays processed data tabularly on screen according to the selection made in Parm_select
Graphical
Displays processed data graphically on screen according to the selection made in Parm_select
Parm_select
Selects moment (magnetization or susceptibility) as a function of field (H), temperature (T), or time (t) for data processing
Output
Select type output: printer or file
Printer
Prints data to hardcopy device. Selects print option
File
Prints data to file. Selects file output option
Addenda
Select/create addenda file
Select
Selects previously generated addenda file
Build
Creates addenda file from data file
Cancel
Cancels previously selected addenda file
Calibration_coeff
Modify/change calibration constant
Parm_select
Selects moment (magnetization or susceptibility) as a function of field (H), temperature (T), or time (t) for data processing

Collection
Display the Collection menu
Sample
Input sample specifications
Susceptibility
Select volume or mass susceptibility and input sample volume or mass
Magnetization
Select volume or mass magnetization and input sample volume or mass
Moment
Select moment (default)
Demagnetization
Enter demagnetization factor (& sample density if processing in terms of mass susceptibility or magnetization)
Calibration-coeff
Modify/change calibration constant
Addenda
Enter addenda file name
Experimental
Set all experimental parameters
Position
Position sample in secondary coil
Top
Specify top coil position
Bottom
Specify bottom coil position
1-Up Coarse
Moves sample up 0.1 inch (0.254 cm)
2-Up fine
Moves sample up 0.01 inch (0.0254 cm)
3-Down fine
Moves sample down 0.01 inch (0.0254 cm)
4-Down Coarse
Moves sample down 0.1 inch (0.254 cm)
Scan
Moves sample from one coil position to the other, and graphs the voltmeter output as a function of time on the screen

Collection (Continued)
Experimental (Continued)

| | | |
|---|---|---|
| H_field | | Selects DC field setting options |
| | MPS_field | Select/Set the DC magnetic field of the superconducting magnet |
| | Profile | Define field profile/control |
| | Discrete | Enter individual field values |
| | Increment | Enter low/high and increment |
| | Loop | Enter field values for hysteresis loop measurements, up to three loops allowed per sequence |
| | Period | Select time duration at a given field, and time between successive measurements |
| | T_change | Select field to be set after the field profile is completed |
| | Edit | Change existing setup |
| | Maintain | On/off toggle to leave field on after the completion of automatic data acquisition |
| | Cancel | Cancel existing setup |
| | Demag_sample | Selection performs demagnetization cycle for elimination of remnant fields |
| | Zero_offset | Selection compensates for any MPS zero-drifts |
| | Small_field | Allows setting small fields with the primary coil and ACS Control Unit |
| | Time_dwell | Select time (in addition to default time settings) for field stabilization |
| Scan | | Enter number of scans per measurement sequence (default = 1) |
| Temp_spec | | Define temperature setup |
| | List | Enter individual points |
| | Incremental | Enter low/high and increment |
| | Sweep | Enter low/high and sweep rate, up to 3 ranges allowed |
| | Drift | No control, select time between measurements |
| | Edit | Change existing setup |
| | Cancel | Cancel existing setup |
| Name | | Enter file name for data storage |
| Calibrate | | Change/adjust calibration constant |
| | Calibrate | Enter moment for sample being tested. Experimentally verify, and store to configuration file |
| | Single-value | Enter new/changed calibration constant |
| Log | | Log data point according to the defined measurement sequence |
| | Begin | Initiates data acquisition process |
| | Tabular | Selects tabular display for real-time feedback |
| | Graphical | Selects graphical display for real-time feedback |
| | Parm_select | Selects option to be displayed. Moment (magnetization or susceptibility) versus field (H), temperature (T), or time (t) |
| | Cancel | Cancels the log sequence |

Auto
Begin automatic data acquisition

| | |
|---|---|
| Begin | Begins data acquisition |
| End | Ends data acquisition |
| Over-ride | Over rides wait period/drift per minute and initiates data taking |
| Real Time | Selects real-time feedback |
| Tabular | Selects tabular mode |
| Graphical | Selects graphical mode |
| Parm_select | Selects option to be displayed. Moment (magnetization or susceptibility) versus field (H), temperature (T), or time (t) |

Collection (Continued)
Temp_ctrl — Set/adjust temperature controller options
Set_Point — Enter temperature setpoint
- 1    Increment +10K
- 2    Decrement −10K
- 3    Increment +1K
- 4    Decrement −1K
- 5    Increment +0.1K
- 6    Decrement −0.1K

Enter Setpt — Input setpoint
Heater_Range — Select heater power range
- Max    Sets to maximum
- 1    Sets to −1
- 2    Sets to −2
- 3    Sets to −3
- Off    Turns off

Gain — Input gain
Derivative — Input derivative/rate
Integral — Input integral/reset
Auto_T — Input setpoint – temperature will be automatically adjusted to that setpoint
Cancel — Cancel and reset to default conditions

Voltmeter — Set/adjust voltmeter control parameters
- Autorange    On/off autoranging toggle
- Select_range    Select range to be used for all data acquisition
- Integration Time    Sets integration on DVM to 1PLC or 100 msec

Recall — Recalls previous experimental configuration

Edit — Adjust/change coil parameters
- Constants    Modify coil parameters
- MPS_rates    Current ramping rates used in charging superconducting magnet
- Save    Save any changes to configuration file

Units — SI/cgs toggle

DOS — Exit to DOS

5.3.3 COMMAND BREAKDOWN AND FUNCTIONAL DESCRIPTION
The following is a complete list of DCM 7000 Software Commands presented in alphabetical order.

Addenda: Analysis Menu.

The following sub-menu is accessed.

Select: Prompts for the name of a previously created addenda file to be used in processing whatever data is contained in the data file selected by File in the Analysis menu.

Build: An Addenda file with the extension ".add" will be created from whatever file has been specified. An addenda file can be created only from data recorded using fixed temperature point acquisition, with at least two applied fields (where one field can be 0-field).

Cancel: Cancels a previously selected addenda file.

Addenda: Sample sub-menu of Collection Menu.

When selected, you will be prompted for the name of a previously created addenda file to be used in processing whatever data is contained in the data file selected by Name in the Experimental Menu.

Analysis: Main Menu.

This is the processing program for processing data contained in data files defined in the Experimental sub-menu of the Collection menu. When selected, the following sub-menu will be displayed.

Begin: Processed data sent to printer or file depending on options selected in Output.

Sample: Allows you to input sample parameters that are to be used in processing the raw moment data.

File: Used to input a file name containing data to be processed.

View: This is a toggle for displaying processed data on the screen.

Output: is for specifying that the processed data be written to a hard copy device or an ASCII file.

Addenda: This allows you to create or select an addenda file to be used when processing data.

Calibration_coeff: This allows you to modify/change the calibration coefficient.

Parm_select: Allows you to specify how the data is processed (i.e., moment, magnetization, or susceptibility as a function of temperature, field, or time).

Auto_T Adjust: Temp_ctrl sub-menu of Collection Menu.

This will automatically warm the system up to a user input temperature at a rate of 3 K/min. When selected, you will be prompted for a setpoint. After typing a setpoint and pressing Enter, the control sensor will be read and the setpoint will be set equal to the control sensor temperature reading and the control setpoint will start to increase at a rate of 3 K/min.

Once the setpoint is reached, the temperature will continue to be controlled at that temperature. Pressing the ESC key will abort the ramping process, and the temperature will be controlled at the setpoint determined when the ESC key was pressed.

| | |
|---|---|
| Auto: | Collection Menu.<br>Starts automatic data acquisition. When selected, the following sub menu is accessed. |
| Begin: | Begins automatic data acquisition process. |
| End: | When selected, you will be prompted with; "Are you sure? Y/N?. If "Y" is selected the automatic data acquisition process will be terminated. Data recorded up to that point will be saved if a file has been specified. To continue with data acquisition, select "N". |
| Over-ride: | During fixed temperature points data acquisition mode, selection of this key will over-ride certain WAITS that are built into the software. Specifically, once a certain setpoint is reached, a WAIT period is entered into to allow the temperature to stabilize and reach equilibrium. The exact length of the WAIT is dependent upon the particular temperature range. Upon completion of the WAIT, a temperature DRIFT CHECK is initiated where the temperature drift per minute is automatically monitored. Once the DRIFT/MIN is below 0.1 K/min the data acquisition/measurement sequence will automatically begin. Selecting Over-ride once will over-ride the designated WAIT period and initiate DRIFT CHECK. Selecting Over-ride again will over-ride this as well and data will then be recorded immediately. |
| Real-Time: | Selection of this activates real-time feedback of processed data. When selected, the following sub-menu is accessed. |

| | | |
|---|---|---|
| | Tabular: | When selected, the data will be displayed tabularly on the screen according to the selection made in Parm_select. If no selection is made, moment data will be displayed. The display format is as follows:<br><br>For data recorded at fixed temperature points as a function of field:<br>    H (SI or cgs)    m (SI or cgs)<br><br>For data recorded at a fixed field as a function of temperature:<br>    T(K)    m (SI or cgs)<br><br>If magnetization is selected in Parm_select, then M (SI or cgs) will be displayed in place of m (SI or cgs). If (m) or (M) versus time (t) is selected in Parm_select, then time (t) in seconds will be displayed in place of T or H. If data has been recorded both as a function of temperature and field (discrete fields), then Parm_select can be used to select whether T or H is displayed. If susceptibility ($\chi$) had been specified in Sample, then $\chi$ (SI or cgs) will be displayed in place of m (SI or cgs). ESC to exit. |
| | Graphical: | When selected, the data will displayed on the screen graphically according to the defined measurement sequence, and the selection made in Parm_select. The possibilities include; moment (or magnetization) versus temperature, moment (or magnetization) versus field, moment (or magnetization) versus time, or susceptibility (at a selected field) as a function of temperature. All scaling is performed automatically. ESC to exit. |
| | Parm_select: | Selection of this permits you to select the way in which the data is displayed on the screen in Real-Time. The choices are; moment, magnetization, or susceptibility versus temperature, field, or time. ESC to exit. |

| | |
|---|---|
| Begin: | Analysis Menu. |
| | Process data is sent to the printer or a file, depending on the options selected in Output. |
| Begin: | Auto sub-menu of Collection Menu. |
| | When Begin is selected, automatic data acquisition is initiated. See Auto. |
| Begin: | Log sub-menu of Experimental sub-menu of Collection Menu. |
| | Initiates data acquisition process and will display the results as they are recorded in the lower left-hand feedback block. ESC to exit. |
| Bottom: | Position sub-menu of Experimental sub-menu of Collection Menu. |
| | This is a toggle for specifying that the sample is positioned in the bottom secondary coil. |
| Build: | Addenda sub-menu of Analysis Menu. |
| | An addenda file will be created with the extension .add from whatever file has been specified. The addenda file can only be created from data logged using fixed temperature points with at least two applied DC fields (where one field can be 0-field). |
| Calibrate: | Calibrate sub-menu of Experimental Menu. |
| | This option assumes a standard sample has been loaded and positioned in the system. Upon selection, the following sequence will be initiated. |
| | 1. A prompt appears for entering the moment of the standard sample being tested. Enter a value and press Enter. |
| | 2. A moment measurement is performed using the number of scans input in the Scan option. |
| | 3. A new calibration coefficient is calculated, displayed on the screen, and then subsequently stored to the configuration file. |
| Calibrate: | Experimental sub-menu of Collection Menu. |
| | When selected, the following sub-menu will appear. |
| | Calibrate: This option assumes that a standard sample has been loaded and positioned in the system and the following sequence is initiated. |
| |     1. A prompt appears for the entering the moment of the standard sample being tested. |
| |     2. A moment measurement is performed using the number of scans input in the Scan option. |
| |     3. A new calibration coefficient is calculated, displayed on the screen, and then subsequently stored to the configuration file. |
| | Single value: When selected, a prompt for changing the currently used calibration coefficient appears. This value will then be stored to the configuration file. |

Calibration_coeff: Analysis Menu.

This will enable you to make changes to the system calibration coefficient when processing data. When selected, you will be prompted for an input. After typing a value, press Enter.

Cancel: This option is contained in five different sub-menus.

1. Addenda sub-menu of Analysis menu.

Selection of this will cancel a previously selected addenda file.

2. Profile sub-menu of H_field sub-menu of Experimental sub-menu of Collection menu.

Selection of this will cancel a previously defined field profile (i.e., discrete fields, hysteresis loops, etc.).

3. Temp_spec sub-menu of Experimental sub-menu of Collection menu.

Selection of this will cancel a previously entered temperature specification.

4. Temp_ctrl sub-menu of Collection menu.

Selection of this will restore the default Temperature Controller parameters.

5. Log sub-menu of Experimental sub-menu of Collection menu

Selection of this will terminate the Log sequence.

Collection: Main Menu.

Collection is used to define the experimental parameters that are to be used when logging data for a particular sample or experiment. When selected, the following sub-menu will be presented.

| | |
|---|---|
| Sample: | Allows you to input sample parameters (i.e., sample volume or mass) that are to be used in the computation of magnetization. |
| Experimental: | Selection of this brings up the experimental set-up menu where experimental parameters are defined for automated data acquisition. |
| Auto: | Acts as a toggle to begin automated data acquisition. |
| Temp_ctrl: | This allows you to interact with the DRC-91CA Temperature Controller via the software. |
| Voltmeter: | This allows you to interact with the voltmeter through the software. |
| Recall: | Allows you to input a previously generated configuration file or experimental set-up. |

NOTE

All of these sub-menus are described in more detail in previous or subsequent sections of this manual.

Constants: Edit sub-menu of Main Menu.

This is used to adjust/modify system constants. When selected, a window of system constants will be displayed. To change a particular system constant, move the cursor to that constant and press Enter. You will then be prompted for an input. After typing a value, press Enter again. ESC to exit.

The system constants that are displayed, and can be changed are:

Field-to-current conversion factor for primary coil.
Calibration coefficient for moment measurement
MPS maximum allowed current
Field-to-current conversion factor for superconducting magnet.

NOTE
The only constants that may need to be adjusted is the calibration coefficient.

Demagnetization: Sample sub-menu of Analysis Menu and
Sample sub-menu of Collection Menu.

This enables you to set a value for the demagnetization factor D. When selected, you will be prompted for an input. Press Enter after typing a value. If a sample mass had been entered (for mass magnetization or mass susceptibility), then you would also be prompted for a sample density.

Demag_Sample: H-Field sub-menu of Experimental sub-menu of Collection Menu.

This function is used to demagnetize the system and sample and eliminate any remnant fields which may be present in the magnet. When selected, the cycle is performed automatically. The routine steps through a process in which the field is ramped to its maximum value and then the field direction is alternately changed and the field amplitude is decreased with each cycle down to the lowest selectable field. The entire cycle takes approximately 5 minutes to complete.

NOTE

- The provision for conducting demagnetization cycles before, and between multiple hysteresis loops (i.e., when using Loop) is built into the software.

- Whenever operation of the system with the magnet is completed, or prior to using the system, Demag_sample should be used to eliminate any stray fields that may be present. Keep in mind that if a sample with "magnetic history" (e.g. a superconductor) is contained in the system when using Demag_sample the sample may be at an unknown point on its hysteresis curve at the completion of the cycle.

Derivative: Temp_ctrl sub-menu of Collection Menu.

This allows you to set the Rate value of the DRC-91CA Temperature Controller. When selected you will be prompted for an input (0 – 9.9). After typing a value, press Enter. The default setting for this parameter is 0.

During automatic data acquisition, this parameter will be set to 0.

Discrete: Profile sub-menu of H_field sub-menu of Experimental sub-menu of Collection Menu.

This routine enables you to enter DC field values individually in order to build your own list of DC fields at which data will be recorded during automated data acquisition.

When selected, you will be prompted for a field input (kAmp/m if SI, kOe if cgs). Input a value and press Enter. A window will be displayed on the screen with this single field value. Continue to enter as many fields as desired (pressing Enter after each entry). Each additional entry will be added to the window. The order in which fields are entered is the order in which the fields will be set, and data recorded, during data acquisition. ESC when completed to exit.

NOTE
Discrete and Incremental can be used together to build a table of discrete field points for fixed point data acquisition.

DOS: Main Menu.

Enables you to exit to the Disk Operating System (DOS). When selected, you will be prompted with the sub-menu "No Yes." Selecting No leaves you in the Main Menu, and selecting Yes exits to DOS.

4 Down Coarse: Position sub-menu of Experimental sub-menu of Collection Menu.

When selected, the sample will be adjusted down 0.1 inch (0.254 cm.) from its current position.

3 Down Fine: Position sub-menu of Experimental sub-menu of Collection Menu.

When selected, the sample will be adjusted down 0.01 inch (0.0254 cm.) from its current position.

Drift: Temp Spec sub-menu of Experimental sub-menu of Collection Menu.

Specifies that data be logged in drift mode where there is no active temperature control (e.g., on cooling), or when the temperature is being controlled at a user defined setpoint selected in Temp_ctrl.

A default interval between successive moment measurements, which depends on the number of scans, will be displayed when this is selected. This value can be changed by entering a new value. Press ESC to use the default value.

| | |
|---|---|
| Edit: | Main Menu.
This feature allows you to change/adjust system constants/default values. When selected the following sub-menu will appear. |
| | Constants: When selected, a window of system constants will be displayed. To change a particular system constant, move the cursor to that constant and press Enter. You will now be prompted for an input. After typing a value, press Enter. The system constants contained in the window are:
    Field-to-current conversion factor for primary coil
    Calibration Coefficient for moment measurement
    MPS maximum allowed current
    Field-to-current conversion factor for superconducting magnet
NOTE
The only constant that may need to be changed/adjusted is the calibration coefficient. |
| | MPS_rates: Parameters that control the ramp rates used in charging the superconducting magnet are displayed. Four ranges are indicated and for each range a rate in amperes per second is given to be used up to the specified absolute current value. Both the ramp rate and current limits can be altered. If only one or two ranges are used, the remaining ranges should have a 0 amp/sec rate specified with the current limit set at the maximum current.
CAUTION
MPS parameters are factory set and should not be altered except by personnel experienced with the operation of superconducting magnets. Damage could result. |
| | Save: This will save any changes made in Constants or MPS_rates to the DCM.DAT file. When selected, you will be prompted with "Are you sure?" Yes saves the new information to the DCM.DAT file, and No does not write the new values to the DCM.DAT file. |
| Edit: | Temp Spec sub-menu of Experimental sub-menu of Collection Menu.
This allows you to edit the temperature specification that was defined using either List, Incremental, or Sweep in the Temp Spec sub-menu. If List or Incremental were used to define the temperature specification, then when Edit is selected the window of discrete temperature points will be displayed. Temperatures can be deleted by moving the cursor to a particular temperature and pressing the Del key.
If the temperature specification is a sweep, when Edit is selected, the sweep window will be displayed. Edit allows you to change sweep rates or nominal temperature spacing. Move the cursor to the rate or spacing you wish to change and press Enter. You can now enter a new value. ESC to exit. |
| Edit: | Profile sub-menu of H Field sub-menu of Experimental sub-menu of Collection Menu.
This allows you to edit the field profile specification which was defined using either Discrete, Incremental, or Loop. If Discrete or Incremental were used to define the field specification, then when Edit is selected, the window of discrete field points will be displayed. Field values can be deleted by moving the cursor to that value and pressing Del. If you wish to enter fields, position the highlight and press INS. You will now be prompted for an input. ESC to exit.
If Loop were used to define the field specification, then selection of Edit will result in the display of the Loop window and allow you to change ramp rates an nominal data point spacing. Move the cursor to the value you wish to change and press Enter. You can now enter a new value. ESC to exit. |

End: Auto sub-menu of Collection Menu.

This is the only way to terminate an experimental run at any point prior to its completion as defined. When selected, you will be prompted with "Yes No." If Yes is selected, the file will be closed and the run aborted. If No is selected, the run will continue as defined.

Enter Setpoint: Set Point sub-menu of Temp Cltr sub-menu of Collection Menu.

This routine sets the temperature setpoint on the DRC-91CA Temperature Controller to a user defined value. When selected, you will be prompted for an input. After typing a value, press Enter.

Experimental: Collection Menu.

This routine is used to set-up or define the experimental conditions or parameters that are used for an automated data acquisition process. When selected, the following sub-menu will be displayed.

| | |
|---|---|
| Position: | This routine is used to position the sample in one of the secondary coils. |
| H_field: | This allows you to select the options available for setting the DC magnetic field. |
| Scan: | This allows you to select the number of scans that will be performed per measurement sequence when acquiring data. |
| Temp_spec: | This is used to define the temperature specifications that are used in automated data acquisition. |
| Name: | This allows you to input a file name to which the data will be stored. |
| Calibrate: | This routine is used to change/modify the system calibration coefficient. |
| Log: | This will log a single measurement sequence as defined in Experimental (i.e., for a defined field profile at a single temperature selected using Enter Setpoint in Temp_ctlr, or with no active temperature control). |

The function of each of these sub-menus is described in more detail in previous or subsequent sections of this manual.

File: Analysis Menu and Output sub-menu of Analysis Menu.

In the Analysis Menu, File is used to load a data file for data processing. When accessed, file names with drive or sub-directory information can be entered and the file will be appropriately accessed. There is no need to specify extensions. If Enter is pressed, the data files contained in the working directory will be displayed in a window. To load a particular file, move the cursor to that file and press Enter. If "a:" is specified, the floppy disk contained in the A drive will be accessed.

In the Output sub-menu, File is used to specify a file to which processed data will be written. When accessed, you will be prompted for a file name. There is no need to specify extensions. Type a file name and press Enter.

Gain: Temp Cltr sub-menu of Collection Menu.

Allows you to change the gain setting of the DRC-91CA Temperature Controller. When selected, you will be prompted for an input (0 – 99). After typing a value, press Enter. The default value is 99 and during automated data acquisition the gain will be set/reset to this value.

Graphical: Real-Time sub-menu of Auto sub-menu of Collection Menu.

This is an on/off toggle. When selected, the (processed) data will be graphically displayed on the screen according to the selection made in Parm_select. All scaling is handled automatically. Depending on the experimental conditions used during data acquisition, and the selection made in Parm_select, the graphical display will show; moment (magnetization, or susceptibility) (vertical axis) versus temperature, field, or time (horizontal axis). ESC to exit.

Graphical: Log sub-menu of Experimental sub-menu of Collection Menu.

This is an on/off toggle. When selected, the (processed) data will be graphically displayed on the screen according to the defined measurement sequence and profile. All scaling is handled automatically. For example, if Loop in Profile were used to define a hysteresis loop measurement either at a single temperature or with no active temperature control, then selection of Log and then Graphical would display the results graphically on the screen as the measurement were performed. The display would show moment (or magnetization) (vertical axis) versus field (horizontal axis). ESC to exit.

Graphical: View sub-menu of Analysis Menu.

This is an on/off toggle. When selected, the processed data chosen using File in analysis will be graphically displayed on the screen according to the selection made using Parm_select. All scaling is handled automatically. Depending on the experimental conditions that were used during automated data acquisition and the selection made in Parm_select, the graphical display will show; moment (magnetization or susceptibility) (vertical axis) versus temperature, field, or time (horizontal axis). ESC to exit.

H_field: Experimental sub-menu of Collection Menu.

This is used to define the field control that is used during automated data acquisition. When selected, the following sub-menu will be displayed.

| | |
|---|---|
| MPS-field: | This is used for setting a single, fixed DC magnetic field of the superconducting magnet. |
| Profile: | This routine enables you to define a field profile (e.g., for recording data as a function of field) at which data will be recorded during automated data acquisition. When selected, the following sub-menu will be displayed. |

| | |
|---|---|
| Discrete: | Allows you to build/define a table of discrete field values. |
| Incremental: | Allows you to build/define a table of discrete field values by selecting a low and high field, and then a field increment. |
| Loop: | This enables you to set-up field loop control (i.e., hysteresis loops) using field sweeps. |
| Period: | Allows you to select the number of data points recorded, and time between data points, for recording moment data versus time. |
| T_change: | This allows you to enter a field which will be set after the completion of a field profile sequence, before the temperature is changed. |
| Edit: | This routine enables you to edit a defined field profile. When selected, the window containing the field set-up will be displayed and field entries can be deleted, added, or changed. |
| Maintain: | This enables you to define a field that will be set at the completion of an automated data acquisition run. |
| Cancel: | This simply cancels a previously defined field profile. |

H_field: (Continued)

- Demag_sample: Used to eliminate any remnant fields which may reside in the system after the application of a high DC magnetic field.
- Zero_offset: Used to more accurately "zero" the zero current setting of the magnet power supply.
- Small_field: Allows setting small DC fields using the ACS control unit and the primary coil.
- Time_dwell: This enables you to input an additional wait period for field stabilization.

NOTE
All of these are described in more detail in previous or subsequent sections of this manual.

---

Heater Range: Temp Cltr sub-menu of Collection Menu.

This allows you to set or change the heater range setting on the DRC-91CA Temperature Controller. When selected, the following sub-menu is displayed.

- MAX: Selection will set the heater range to maximum power.
- 1_-2: Selection will set the heater range to -1.
- 2_-2: Selection will set the heater range to -2.
- 3_-3: Selection will set the heater range to -3.
- OFF: Selection will turn the power off.

The heater range is automatically set when in automatic data acquisition mode.

---

Incremental: Temp Spec sub-menu of Experimental sub-menu of Collection Menu.

This allows you to define discrete temperature points for fixed point data acquisition by entering them incrementally. When selected, you will be prompted for a low temperature value, then a high, and finally an increment (e.g., 10K to 100K in 5K increments). The table of selected values will be displayed on the screen as a window. To input another range, press Enter. To exit, press ESC.

NOTE
Enter List and Incremental can be used together to build a table of discrete temperature points for fixed temperature point acquisition.

---

Incremental: H Field sub-menu of Experimental sub-menu of Collection Menu.

This allows you to define discrete field points for fixed field data acquisition by entering them incrementally. When selected, you will be prompted for a first field value, then a second range value, and finally an increment value (e.g. 0 kOe (or 0 kAmp/m) to 10 kOe (or 800 kAmp/m) in 1 kOe (or 80 kAmp/m) increments). The table of selected values will be displayed on the screen as a window. To input another range, press Enter. To exit, press ESC.

NOTE
Discrete and Incremental can be used together to build a table of discrete field points for fixed field point acquisition.

---

Integral: Temp Cltr sub-menu of Collection Menu.

Allows you to change the Reset setting of the DRC-91CA Temperature Controller. When accessed, you will be prompted for an input (0 – 99). After typing a value, press Enter. The default value is 0 and during automated data acquisition the reset will be set/reset to 0.

Integration_time: Voltmeter sub-menu of Collection Menu.

Used to set the Digital Voltmeter (DVM) integration time to either 1 power line cycle (PLC) or 100 milliseconds.

Label: Sample sub-menu of Analysis Menu.

Allows you to input a label which will be printed at the head of a hardcopy of your processed data.

List: Temp Spec sub-menu of Experimental sub-menu of Collection Menu.

This routine enables you to enter temperatures individually in order to build your own list of temperatures at which data will be recorded during automated data acquisition.

When selected, you will be prompted for a temperature input. Input a value and press Enter. A window will be displayed on the screen with this single temperature value. Continue to input as many temperature as desired (pressing Enter after each entry). Each additional entry will be added to the window. The order in which temperatures are entered is not important. They will be automatically ranked in ascending order upon entry. ESC when completed to exit.

NOTE

Enter List and Incremental can be used together to build a table of discrete temperature points for fixed temperature point data acquisition.

Log: Experimental sub-menu of Collection Menu.

Selection of this will record a single measurement sequence as defined, and if specified, also execute a field profile at the current temperature. When automatic temperature control and variable temperature are required as specified in the Temp Spec menu, the Auto menu should be accessed. When selected, the following sub-menu will be displayed.

- Begin: This actually initiates the data acquisition process, and will display the results as they are recorded in the lower left-hand feedback block. ESC to exit.

- Tabular: This is an on/off toggle. When selected, the measurement results will be displayed tabularly on the screen. The display format is:

H(kOe or kAmp/m)   m (emu or A m²)

If a sample volume or mass were input, m would be replaced by the magnetization (M) or susceptibility ($\chi$) (depending on selection made in Sample). ESC to exit.

- Graphical: This is an on/off toggle. When selected, the measurement results will be displayed graphically on the screen. The vertical axis will be moment (magnetization or susceptibility), and the horizontal axis will be field (H). All scaling is handled automatically. ESC to exit.

- Parm_Select: Selects analysis display parameters.

- Cancel: Terminate the data acquisition.

This data can be written to a field specified using Name. If no field name is specified it will be written to TEMPFILE.DAT and TEMPFILE.CFG. To abort the Log sequence, select Cancel.

CAUTION

If Log is used successively, and no file specification is made, the contents of TEMPFILE.DAT will be overwritten.

Loop: Profile sub-menu of H Field sub-menu of Experimental sub-menu of Collection Menu.

For the generation of hysteresis loops, or field sweeping (i.e., any field control not involving discrete field points), this routine should be used. When selected, you will be prompted for the first of four field entries. Type in a value and press Enter. If you typed in a 0, you will be prompted as to whether or not you wish to have a demagnetization cycle performed prior to starting the loop. Respond with a Y (for Yes), or N (for No). A window with the following headings will be displayed on the screen.

| Loop Num | Field #1 | Field #2 | Field #3 | Field #4 | Rate (/min.) | Spacing | Min. Spacing | Number Data Pts |
|---|---|---|---|---|---|---|---|---|

You will then be prompted for the second field entry. Enter a value and press Enter. You will likewise be prompted for the third, and forth field entries respectively. After entering the last field entry, you will be prompted for a rate. Enter a value and press Enter.

For example, if you wished to set up a hysteresis loop from 0 to 10 kOe (800 kAmp/m), to −10 kOe (800 kAmp/m), and back to 10 kOe (800 kAmp/m) at a rate of 1 kOe/min (80 kAmp/m per min) then you would enter: 0, and either Y or N (for the demag. cycle), then +10 kOe (or +800 kAmp/m), −10 kOe (or −800 kAmp/m), +10 kOe (or +800 kAmp/m), and finally 1.0 kOe/min. (or 80 kAmp/m/min.).

At this point the window would contain the following information:

| Loop Num | Field #1 | Field #2 | Field #3 | Field #4 | Rate (/min.) | Spacing | Min. Spacing | Number Data Pts |
|---|---|---|---|---|---|---|---|---|
| 1 | 0, D[1] | +10 | −10 | +10 | 1 | 0.5 | 0.5 | 100 |

[1] A zero will be displayed if N was selected at the prompt for the execution of the demag. cycle, and a D will be displayed if the response had been Y.

The Spacing and Min. Spacing are determined from the imputed loop parameters, and the default condition that approximately 100 data points per loop be recorded. This default condition serves two purposes. It reduces/minimizes wear on the sample probe seal, and eliminates the possibility of accumulating an unwieldy number of data points.

For more or less data the Rate or Spacing can be changed by moving the cursor to that position and pressing Enter. An imputed value for Spacing must be > Min. Spacing.

Up to 3 loops can be set-up/defined. Press Enter to define a second loop and proceed as outlined above, or ESC to exit.

NOTE

If it is desired to simply sweep the field from one value to another while recording moment data, Loop should also be used. For example, assume that you wish to record data as the field is swept from 0 to 1 kOe (or 80 kAmp/m) at 0.2 kOe/min (or 16 kAmp/m/min), then input 0 (and Y or N for the demag cycle). Then 1 kOe (or 80 kAmp/m) for the second field entry. For the third and fourth field entry prompts, simply press ESC. Then enter 0.1 kOe (or 16 kAmp/m/min) at the Rate prompt. Again, the 100 data point default (assuming the range/rate combination will permit this many data points to be recorded) will be adhered to and data will be recorded as the field is swept. Once the sweep has been completed, the field will be set to 0 or whatever has been specified in T_change.

Magnetization: Sample sub-menu of Analysis Menu and Sample sub-menu of Collection Menu.

This is used to specify that magnetization be computed from moment data. When selected, the following sub-menu will be displayed.

Volume: When selected, you will be prompted for a sample volume. After typing a value, press Enter.

Mass: When selected, you will be prompted for a sample mass. After typing a value, press Enter. If a non-zero demagnetization factor had been previously defined, you would also be prompted for a sample density.

| | |
|---|---|
| Maintain: | Profile sub-menu of H Field sub-menu of Experimental sub-menu of Collection Menu. |
| | This is an on/off toggle that will leave the DC field set to whatever value it was set to at the termination of data acquisition. For example, if zero-field-cooled (ZFC) data is being recorded on warming, and after this is completed it is desired to record field-cooled (FC) data, then Maintain will automatically leave the field on at the completion of the run, as the system cools back down. |
| Mass: | Susceptibility sub-menu of Sample sub-menu of Analysis Menu and Magnetization sub-menu of Sample sub-menu of Collection Menu. |
| | Specifies that mass susceptibility is to be computed. When selected, you will be prompted for a sample mass. After typing a value, press Enter. If Demagnetization had been previously selected to specify a non-zero D, then you will also be prompted for a sample density. |
| Mass: | Sample sub-menu of Collection Menu. |
| | Selection of this specifies that mass magnetization is to be computed from moment data. When selected, you will be prompted for a sample mass. After typing a value, press Enter. If Demagnetization had been previously selected to specify a non-zero D, then you will also be prompted for a sample density. |
| MAX: | Heater Range sub-menu of Temp Cltr sub-menu of Collection Menu. |
| | Selection will set the heater range to maximum power. |
| Moment: | Sample sub-menu of Analysis Menu and Sample sub-menu of Collection Menu. |
| | This is an on/off toggle for specifying that the data be processed in terms of magnetic moment. Moment is the default processing condition. |
| MPS_field: | H Field sub-menu of Experimental sub-menu of Collection Menu. |
| | This is used for setting the DC magnetic field of the superconducting magnet. When selected, you will be prompted for an input. Enter a value (kOe or kAmp/m), and press Enter. The field will then be automatically adjusted to, and stabilized at the selected field. ESC to exit. |
| MPS_rates: | Edit sub-menu of Main menu. |
| | Parameters that control the ramp rates used in charging the superconducting magnet are displayed. Four ranges are indicated and for each range a rate in amperes per second is given to be used up to the specified absolute current value. Both the ramp rate and current limits can be altered. Of only one or two ranges are used, the remaining ranges should have a 0 amp/sec rate specified with the current limit set at the maximum current. |
| | CAUTION |
| | MPS parameters are factory set and should not be altered except by personnel experienced with the operation of superconducting magnets. Damage could result. |
| Name: | Experimental sub-menu of Collection Menu. |
| | This allows you to specify a data file to which the data logged will be written. When selected, you will be prompted for a file name with no extensions. After typing a file name, press Enter. |
| | If no file name is specified, the data will be written to TEMPFILE.DAT and TEMPFILE.CFG. If the file name selected already exists, you will be prompted for another file name. If no new name is specified, the new data will overwrite the data currently contained in the file. |

Off: Heater Range sub-menu of Temp Cltr sub-menu of Collection Menu.

Selection will turn the heater power off.

Output: Analysis Menu.

This option allows you to specify that the processed data be dumped to a hard copy device or written to a file (ASCII file format). When selected, the following sub-menu appears.

Printer: On/off toggle to specify that the data be printed to a hardcopy device. Depending on the experimental parameters that were used to record data, and the selection made in Sample and Parm_select, the data will be printed out in a two column format (i.e., m versus T, m versus H, $\chi$ versus T, etc.) with appropriate headings.

File: When selected, you will be prompted for a file name (no extensions). After typing the file name, press Enter.

The files are created in ASCII file format and consist of columns separated by a single white space (i.e., m[space]T, m[space]H, $\chi$[space]T, etc.).

Override: Auto sub-menu of Collection Menu.

During fixed temperature point data acquisition mode, selection of this key will override certain WAITS that are built into the software. Specifically, once a certain setpoint is reached, a WAIT period is entered into to allow the temperature to stabilize and reach equilibrium. The exact length of the WAIT is dependent on the particular temperature range. Upon completion of the WAIT, a DRIFT CHECK is initiated where the drift per minute is automatically monitored. Once this DRIFT/MIN is below 0.1K/min, the data acquisition/measurement sequence will automatically begin. Selecting Override once will override the designated WAIT and initiate the DRIFT CHECK, and selecting it again will override this as well and data will be recorded immediately.

While the temperature is being adjusted from one setpoint to another, Override can be selected to record data at some intermediate temperature. When Override is selected, the temperature ramping will cease, and the above mentioned WAIT period will be initiated.

Parm_select: Analysis Menu and Real Time sub-menu of Auto of Collection Menu and Log sub-menu of Experimental sub-menu of Collection Menu This routine is used to select the way in which the data is displayed when using real-time graphics or tabular display. Depending on the experimental parameters used when recording data, the possibilities include; moment, magnetization, or susceptibility vs. temperature, field, or time.

When selected, a window will appear showing the options available contingent on the experimental set-up. Move the cursor to the particular combination you wish to view and press Enter.

If data was recorded such that there was only one way in which to view the data (e.g., moment vs. field at one temperature, susceptibility vs. temperature at one field, etc.), then when Parm_select is selected, a message to this effect will be displayed on the screen. If data was recorded such that a selection is warranted (e.g., magnetization vs. temperature and field), then the window will contain two selections; magnetization vs. temperature, and magnetization vs. field. After selecting one of these (e.g., magnetization vs. temperature), an additional window will be displayed. In this case, a window will be displayed which will prompt you to select a field. A window will then be displayed to show the selections you have made. Press ESC to acknowledge.

Period: Profile sub-menu of H Field sub-menu of Experimental sub-menu of Collection Menu.

Permits selection of experimental parameters to be used when recording magnetization data as a function of time. A DC field must first be selected using MPS_field, or a table of discrete fields defined using Discrete or Incremental, and a temperature specification must be made using either List or Incremental.

When Period is selected, you will be prompted for the number of scan sequences. Note that this is not the number of scans. For example, if up in the scan feature in the Experimental sub-menu of the Collection menu you defined the number of scans (measurement sequence) as 10, then in Period you defined the desired number of scan sequences as 5, you would get 5 scan sequences with each scan sequence performing and averaging over 10 scans.

This is significant because after defining the desired number of scan sequences, you will be prompted for the number of seconds between each. Note that a scan takes approximately 15 seconds. Therefore, 10 scans will take about 150 seconds. This is in addition to the time you will now be defining between each scan sequence.

During automated data acquisition, the field will be set and the system default waits, and any additional user defined waits (i.e., Time_dwell) will be initiated. After the completion of these waits, the moment will be recorded as a function of time according to the parameters input in Period. If a table of field values has been defined, the field will then be incremented to the next value and the process will start anew. If a table of temperature values has also been defined using either List or Incremental, then after the completion of the field profile, the temperature will be adjusted to the next value and after the temperature stabilization period, the process will start anew.

If multiple scans are used to record the moment, then the time interval between measurements extends from the end of one scan sequence to the beginning of the next scan sequence.

ESC to exit.

---

Position: Experimental sub-menu of Collection Menu.

This routine is used to position the sample in one of the two secondary coils. When accessed, the following sub-menu will be displayed.

| | |
|---|---|
| Top: | Toggle that specifies the sample is positioned in the top secondary coil. |
| Bottom: | Toggle that specifies the sample is positioned in the bottom secondary coil. |
| 1 Up/Coarse: | Will move the sample up 0.1 inch (0.254 cm.) from its current position. |
| 2 Up/Fine: | Will move the sample up 0.01 inch (0.0254 cm.) from its current position. |
| 3 Down/Fine: | Will move the sample down 0.01 inch (0.0254 cm.) from its current position. |
| 4. Down/Coarse: | Will move the sample down 0.1 inch (0.254 cm.) from its current position. |
| Scan: | This feature is used to position the sample. When selected, a half scan will be performed, and the actual voltage signal measured will be graphed on the screen. Messages will appear on the screen which indicate in which direction the sample should be moved (i.e., up or down) to yield a symmetric voltage signal (the voltage signal will be perfectly symmetrical when the sample is properly positioned). Use the coarse and fine adjust keys to move the sample in the proper direction, and initiate the Scan sequence again. Repeat this iteration until the sample is properly positioned (i.e., until a symmetric voltage signal is obtained). |

Printer: Output sub-menu of Analysis Menu.

This is an on/off toggle. When selected the processed data will be printed to a hard copy device.

Profile: H Field sub-menu of Experimental sub-menu of Collection Menu.

This routine is used to define/set-up the field profile/control that is to be used during an automated data acquisition run. When selected, the following sub-menu will be displayed.

| | |
|---|---|
| Discrete: | This is used to input discrete field values for creating a field table at which data will be recorded. |
| Incremental: | This is for the selection of fields used for creating a field table, entered incrementally, to be used in automated data acquisition. |
| Loop: | This enables you to set-up field loop control (i.e., hysteresis loops), and field sweeps for recording data at discrete temperatures. |
| Period: | This is used to specify parameters that are to be used when recording magnetization data as a function of time (i.e., time duration at a given field, and time between measurements). |
| T_change: | This allows you to input a field value that will be set after the completion of a field profile, prior to adjustment of the temperature. The temperature will be adjusted at this field setting. |
| Edit: | Selection of this enables you to edit previously defined field control parameters. |
| Maintain: | This is an on/off toggle that will leave the field set to a user defined value after the completion of an automated data acquisition run (e.g., for recording field-cooled magnetization data after the completion of a zero-field-cooled automated data acquisition run). |
| Cancel: | This allows you to cancel a previously defined field profile/control. |

NOTE

All of these sub-menus are described in more detail in previous or subsequent sections of this manual.

Real Time: Auto sub-menu of Collection Menu.

This feature will display, either tabularly or graphically, the measured data on the screen in real-time (i.e., as it is being recorded). What is actually displayed is dependent on the experimental parameters that were used to record data, and also the selection made in Parm_select. When selected, the following sub-menu will be displayed.

Tabular: This is an on/off toggle. When on, the data will be displayed on the screen in the following format.

If moment (magnetization or susceptibility) vs. temperature were recorded/selected in Parm_select.

T(K)    m (or M) (SI or cgs)

If moment (magnetization or susceptibility) vs. field were recorded/selected in Parm_select.

H(SI or cgs)    m (or M) (SI or cgs)

If moment (magnetization or susceptibility) vs. time were recorded/selected in Parm_select.

t (mins.)    m (or M) (SI or cgs)

You can scroll through the data using the Home/End keys or the PgUp/PgDn keys. ESC to exit.

Graphical: This is an on/off toggle. When on, the data will be displayed on the screen as a graph or plot of moment (magnetization or susceptibility) vs. either temperature, field, or time (again, depending on the experimental parameters used in recording data, and also on the selection made in Parm_select). Moment (magnetization or susceptibility) will be presented on the vertical axis, and either temperature, field, or time will be presented on the horizontal axis. All scaling is fully automated. ESC to exit.

Parm_select: This is for the selection of parameters that are to be displayed either graphically or tabularly when using the real-time feedback feature. Depending on the experimental parameters used when recording data, the possibilities include; moment (magnetization or susceptibility) vs. temperature, field, or time. ESC to exit.

Recall: Collection Menu.

This routine enables you to load a previously generated configuration file. This is useful when samples are often run using the same experimental conditions or parameters. When selected, you will be prompted for a field name (no extensions). After typing a file name, press Enter. Changes to the experimental configuration can then be made through the software if required.

Sample: Analysis Menu.

This enables you to input sample parameters that are used in calculations from raw moment data. When selected, the following sub-menu is displayed.

Susceptibility: Allows you to input volume or mass susceptibility. When selected, the following sub-menu is displayed.

- Vol.: Selection of this specifies that volume susceptibility is to be computed from moment data. When selected, you will be prompted for a sample volume. Input a value and press Enter.

- Mass: Selection of this specifies that mass susceptibility is to be computed from moment data. When selected, you will be prompted for a sample mass. Input a value and press Enter. If Demagnetization had been previously selected to specify a non-zero demagnetization factor, then you will also be prompted for a sample density.

Demagnetization: This is used to input a non-zero demagnetization factor. When selected you will be prompted for a demagnetization factor. Input a value and press Enter. If mass susceptibility or magnetization had been previously selected, you will also be prompted to input a sample density.

Moment: Selection of this specifies that raw data or moment data is to be considered. This is the default condition.

Magnetization: Allows you to input volume or mass magnetization. When selected, the following sub-menu is displayed.

- Vol.: Selection of this specifies that volume magnetization is to be computed from moment data. When selected, you will be prompted for a sample volume. Input a value and press Enter.

- Mass: Selection of this specifies that mass magnetization is to be computed from moment data. When selected, you will be prompted for a sample mass. Input a value and press Enter. If Demagnetization had been previously selected to specify a non-zero demagnetization factor, then you will also be prompted for a sample density.

Label: Allows you to enter a sample label that will be printed on the hard copy printout of the processed data when the Printer option in Output is selected. When selected, you will be prompted for an input. Type in an appropriate sample label, and press Enter.

Sample: Collection Menu.

This enables you to input sample parameters that are used in any computations from raw moment data. When selected, the following sub-menu will appear.

- Susceptibility: Allows you to input volume or mass susceptibility. When selected, the following sub-menu will appear.

- Vol.: Selection of this specifies that volume susceptibility is to be computed from moment data. When selected, you will be prompted for a sample volume. Input a value and press Enter.

- Mass: Selection of this specifies that mass susceptibility is to be computed from moment data. When selected, you will be prompted to input a sample mass. Input a value and press Enter. If Demagnetization had been previously selected to specify a non-zero demagnetization factor, then you will also be prompted for a sample density.

- Demagnetization: This is used to specify a non-zero demagnetization factor. When selected, you will be prompted for a demagnetization factor. Input a value and press Enter. If mass susceptibility or magnetization had previously been selected, you will also be prompted to input a sample density.

- Moment: Selection of this specifies that raw data or moment data is to be considered. This is the default condition.

- Magnetization: Allows you to input volume or mass magnetization. When selected, the following sub-menu is displayed.

- Vol.: Selection of this specifies that volume magnetization is to be computed from moment data. When selected, you will be prompted for a sample volume. Input a value and press Enter.

- Mass: Selection of this specifies that mass magnetization is to be computed from moment data. When selected, you will be prompted for a sample mass. Input a value and press Enter. If Demagnetization had been previously selected to specify a non-zero demagnetization factor, you will also be prompted for a sample density.

- Addenda: This enables you to input an addenda file to be used in processing the data in real time. When selected, you will be prompted for an addenda file name (no extensions). Enter a valid file name, and press Enter.

Save: Edit sub-menu of Main Menu.

This enables you to save any changes that were made in Constants or MPS_rates to the DCM.DAT file. When selected, you will be prompted with "Are You Sure? Yes No." If Yes is selected, the new information will be written to DCM.DAT. If No is selected, the new information will not be written to DCM.DAT.

Scan: Position sub-menu of Experimental sub-menu of Collection Menu.

This feature is used to position the sample within one of the secondary coils. When selected, a half-scan will be performed and the actual voltage signal will be graphed on the screen. Messages are displayed on the screen which indicate in which position the sample should be moved (i.e. up or down) to make the voltage curve more symmetrical. When the voltage curve is symmetrical, then the sample is properly positioned. Adjust the position of the sample using the coarse and fine up/down keys, and then select Scan again. Repeat this process until the sample has been positioned well enough to yield a symmetric voltage signal.

Scan: Experimental sub-menu of Collection Menu.

This simply prompts for the number of scans to be used in the moment measurement. The default is one scan.

Select: Addenda sub-menu of Analysis Menu.

This selects the addenda file to be used in processing the data in Analysis. When selected, you will be prompted for an addenda file name (no extensions). After typing a valid file name, press Enter.

Select_range: Voltmeter sub-menu of Collection Menu.

Selection of this allows you to set the range of the voltmeter at which data will be recorded. To leave the voltmeter on this range during automated data acquisition, Autorange must be selected to disable the autoranging feature.

Set Point: Temp Cltr sub-menu of Collection Menu.

This routine enables you to adjust or change the temperature setpoint of the DRC-91CA Temperature Controller. When selected, the following sub-menu will be displayed.

| | |
|---|---|
| 1 +10: | Increments the temperature setpoint +10 K from its current value. |
| 2 -10: | Decrements the temperature setpoint -10 K from its current value. |
| 3 +1: | Increments the temperature setpoint +1K from its current value. |
| 4 -1: | Decrements the temperature setpoint -1K from its current value. |
| 5 +0.1: | Increments the temperature setpoint +0.1K from its current value. |
| 6 -0.1: | Decrements the temperature setpoint -0.1K from its current value. |

Enter Setpoint: Sets the setpoint at a user defined value. When selected, you will be prompted for an input. Input a setpoint (selectable to within 0.1K) and press Enter.

Single_value: Calibrate sub-menu of Experimental sub-menu of Collection Menu.

When selected, a prompt for changing the currently used calibration coefficient appears. Input a value and press Enter. The new calibration coefficient will be stored to the configuration file.

Small_field: H Field sub-menu of Experimental sub-menu of Collection Menu.

This routine is used for setting "small" DC bias fields using the ACS control unit and the primary coil. When selected, you will be prompted for an input (0 to ±1040 A/m or ±13 Oe RMS). Input a value and press Enter.

Susceptibility: Sample sub-menu of Analysis Menu and Sample sub-menu of Collection Menu.

Allows you to select volume or mass susceptibility.

Sweep: Temp Spec sub-menu of Experimental sub-menu of Collection Menu.

This routines allows you to set the temperature sweep parameters that are to be used during an automated data acquisition sequence. When selected, you will be prompted for a lower temperature, a higher temperature, and a temperature sweep rate (0.1 to 3 K/min) (e.g., 10 to 100 K @ 1 K/min). The following information will be displayed on the screen in a window.

| Range Number | Low Temp(K) | High Temp(K) | Rate (K/min.) | Spacing (K) | Minimum Spacing | Number of Data Points |
|---|---|---|---|---|---|---|

One of the parameters displayed will be temperature spacing. This is the approximate default spacing according to the defined measurement sequence (i.e. minimum spacing). The cursor will be on the sweep rate entry. If you desire to change the sweep rate, Simply press Enter and input a new value. If you desire to change the temperature spacing, move the cursor to that value and press Enter and then input a new value (with the condition that the new value be greater than or equal to the default value).

The software provides for up to three different sweep ranges. If you desire only one sweep range, press ESC to exit. If you desire a second sweep range (& third), press Enter. Now you will be prompted for an ending temperature for the second sweep range (the starting temperature of the second sweep range is the ending temperature of the first, & so on), and a sweep rate. The new information will be added to the window, and changes to the rate and spacing can be made as outlined above. To input a third range, press Enter and continue as outlined above. Press ESC at any time to exit.

---

T_change: Profile sub-menu of H Field sub-menu of Experimental sub-menu of Collection Menu This routine is used to select a field that will be set at the completion of a measurement profile, before the temperature setpoint is changed or adjusted. When selected, you will be prompted for a value. Input a value, and press Enter. The default value for this is 0-field.

---

Tabular: View sub-menu of Analysis Menu, Real Time sub-menu of Auto sub-menu of Collection Menu, and Log sub-menu of Experimental sub-menu of Collection Menu The purpose of Tabular is the same in all sub-menus. When selected, the processed data will be displayed on the screen in tabular format according to the defined measurements sequence and the selection made using Parm_select.

---

Temp Cltr: Collection Menu.

This routine allows you to set, modify or change a number of parameters on the DRC-91CA Temperature Controller. When selected, the following sub-menu will be displayed.

Setpoint: For selection of control setpoint on Temperature Controller.

Heater Range: For selection of heater range on Temperature Controller.

Gain: For selection of gain setting on Temperature Controller.

Derivative: For selection of rate setting on Temperature Controller.

Integral: For selection of reset setting on Temperature Controller.

Auto T: For selection of a setpoint that will then be automatically warmed to at a rate of 3 K/min and subsequently controlled at.

NOTE

A more detailed description of each of these functions can be found in preceding or subsequent sections of this manual.

Temp Spec: Experimental sub-menu of Collection Menu.

This routine enables you to define the temperature specifications used during automated data acquisition. When selected, the following sub-menu will be displayed.

| | |
|---|---|
| List: | For selection of individual temperature points used in automated data acquisition. |
| Incremental: | This is for selection of temperatures, entered incrementally, to be used in automated data acquisition. |
| Sweep: | Enables user to enter temperature sweep parameters used in automated data acquisition. |
| Drift: | For selection of drift (with no active temperature control or while controlling at user defined temperature point) mode during data acquisition. |
| Edit: | Allows the user to delete temperature from list defined by Enter List or Incremental and also for changing sweep rates or temperature spacings in sweep mode. |
| Cancel: | Used to cancel a previously defined temperature specification. |

NOTE

A more detailed description of each of these sub-menus is contained in previous or subsequent sections of this manual.

---

Time_dwell: H Field sub-menu of Experimental Menu.

This is used to input a field stabilization time period, in addition to the default time periods contained in the software. When selected, you will be prompted for an input (in seconds). Type in a value and press Enter. Whenever a field change occurs during data acquisition, the system will remain idle for the default wait period plus the Time Dwell. This will allow extra time for field stabilization prior to recording data. The default value of Time Dwell is 0 seconds.

---

Top: Position sub-menu of Experimental sub-menu of Collection Menu.

This is a top coil toggle that allows you to specify that the sample is positioned in the top secondary coil.

---

1 Up Coarse: Position sub-menu of Experimental sub-menu of Collection Menu.

Selection of this will move the sample up 0.1 inch (0.254 cm) from its current position.

---

2 Up Fine: Position sub-menu of Experimental sub-menu of Collection Menu.

Selection of this will move the sample up 0.01 inch (0.0254 cm) from its current position.

---

Units: Main Menu.

This is simply an SI/cgs units toggle.

View: Analysis Menu.

This enables you to specify whether the processed data is displayed tabularly or graphically on the screen. When selected, the following sub-menu will be displayed on the screen.

- Tabular: Selecting this will cause the data to be displayed on the screen tabularly according to the experimental parameters used during data acquisition, and the selection made in Parm_select. The display will consist of a two column format showing; moment (or magnetization or susceptibility) vs. either temperature, field, or time.

- Graphical: Selecting this will cause the data to be displayed graphically on the screen according to the experimental parameters used during data acquisition, and the selection made in Parm_select. The result will be a graph or plot of; moment (or magnetization or susceptibility) (vertical axis) vs. either temperature, field, or time (horizontal axis).

ESC to exit.

---

Voltmeter: Collection Menu.

This allows you to disable the auto-ranging feature of the voltmeter or to adjust the sensitivity range of the voltmeter. When selected, the following sub-menu will appear.

- Autorange: This is an on/off toggle for disabling the auto-ranging feature of the voltmeter.

- Select_range: This allows you to choose which sensitivity range is used during automated data acquisition.

- Integration_time: Used to set the Digital Voltmeter (DVM) integration time to either 1 power line cycle (PLC) or 100 milliseconds.

---

Volume: Susceptibility sub-menu of Sample sub-menu of Analysis Menu and Magnetization sub-menu of Sample sub-menu of Analysis Menu.

A request for a sample volume occurs in both the Susceptibility and Magnetization sub-menus where its selection specifies that volume susceptibility and volume magnetization, respectively, is to be computed from moment data. In either case, when selected you will be prompted for a sample volume. Input a value and press Enter.

---

Volume: Sample sub-menu of Collection Menu.

Selection of this specifies that volume magnetization or suscepibility is to be computed. When selected, you will be prompted for a sample volume. Input a value and press Enter.

---

Zero_Offset: H Field sub-menu of Experimental sub-menu of Collection Menu.

This feature is used to adjust the current output of the MPS to account for zero drifts in the power supply output due to fluctuations in the operating environment (e.g., room temperature variations). The "zeroing" is accomplished automatically upon selection.

When using this feature, the output current (at zero current) is read (i.e., $I_0$) and the current is then set to $-I_0$. In addition, any field that is subsequently set using the MPS is corrected by this $I_0$. This feature is particularly useful for operation at low fields, and also to obtain the best accuracy in the resultant DC field.

What is claimed is:

1. A method of automatically characterizing ac and dc magnetic properties of a sample comprising the following steps:
   closely thermally linking a sensing coil arrangement to the sample;
   varying, using computer control, the temperature of the sensing coil arrangement and thereby also the temperature of the sample closely thermally linked thereto;
   automatically measuring, by coupling electrical signals to/from the sensing coil arrangement, an ac susceptibility characteristic of the sample; and
   automatically measuring, by coupling electrical signals to/from the sensing coil arrangement, a dc magnetization characteristic of the sample,
   wherein said measuring steps are automatically performed successively under said computer control without thermally unlinking said sample from said sensing coil arrangement.

2. A method as in claim 1 wherein said dc magnetization characteristic measuring step comprises using a computer to automatically move said sample from the center of a first sensing coil to the center of a second sensing coil to provide substantially symmetric signal measurements.

3. A method as in claim 1 wherein said dc magnetization characteristic measuring step comprises automatically moving said sample relative to said sensing coil arrangement under computer control.

4. A method as in claim 1 wherein said dc magnetization characteristic measuring step comprises digitally integrating, substantially in real time, sensing coil voltage over time to determine total magnetic flux change and correcting the resulting integral with a calibration factor to yield a dc moment value.

5. A method as in claim 1 further including the step of calibrating said ac characteristic measurement and said dc characteristic measurement with a common calibration.

6. A method as in claim 1 wherein said dc magnetization characteristic measuring step comprises integrating at least one voltage over time with an integrating digital voltmeter.

7. A method as in claim 1 wherein said ac magnetization characteristic measuring step comprises moving said sample relative to said sensing coil arrangement so as to magnetically couple said sample alternately to a first sensing coil and to a second sensing coil during said ac susceptibility measuring step.

8. A method as in claim 1 wherein at least one of said measuring steps comprises sampling and averaging several scans per measurement point.

9. A method as in claim 1 further including displaying a computer controlled display screen providing frequency, amplitude and harmonic measurement selection.

10. A method as in claim 1 further including performing multiple temperature-dependent susceptibility sequences at different field, followed by several dc measurements at different temperatures, for a single sample in a common measurement sequence without thermally unlinking said sample from said sensing coil arrangement.

11. A method as in claim 1 further including allowing the user to program a computer to set up a sequence of measuring conditions selected from the set of: cooling conditions, temperature conditions, field conditions, ac drive field, measurement type, harmonics, and real time plotting.

12. A method as in claim 1 wherein each of said measuring steps includes the step of recording measurement data in a computer data file.

13. A magnetic measuring system for measuring the ac and dc magnetic characteristics of a sample at cryogenic temperatures, said system comprising:
   a cryogenic chamber;
   at least one sensor coil arrangement disposed within said chamber, said sensor coil arrangement including a primary coil and plural, substantially balanced sensing coils;
   a computer;
   means for mounting said sample within said chamber and for moving said sample relative to said sensor coil arrangement under control of said computer;
   means for applying a constant magnetic field to said sample to make dc. magnetic characteristic measurements; and
   means, coupled to said sensing coils, for successively measuring dc magnetic characteristics and ac magnetic characteristics of said sample without requiring said sample to be removed from said chamber,
   said system further including ac applying means for selectively coupling an ac excitation signal to said primary coil during said ac magnetic characteristic measurements.

14. A system as in claim 12 wherein said mounting and moving means comprises a computer-controlled electric motor for automatically moving said sample from one to another of said plural sensing coils for at least said dc magnetic characteristic measurements.

15. A system as in claim 13 wherein sensor coil arrangement includes a sapphire coil form, said plural sensing coils being wound on said sapphire coil form.

16. A system as in claim 13 wherein said sensor coil arrangement comprises a longitudinally separated detection coil set comprising said plural sensing coils with primary coil wound around said set.

17. A system as in claim 13 wherein each of said plural sensing coils is made of copper.

18. A system for measuring ac and dc magnetic characteristics of a sample, said system comprising:
   a chamber;
   a dc field coil magnetically coupled to said chamber;
   at least one sensor coil arrangement disposed within said chamber, said sensor coil arrangement including an ac field coil and at least one sensing coil;
   electronics coupled to said dc field coil and to said sensor coil arrangement, said electronics comprising:
   (a) an ac signal processing arrangement that applies, during an ac measurement, an ac signal to said ac field coil and measures ac magnetic characteristics of said sample in response to signals received from said sensing coil,
   (b) a dc signal processing arrangement that applies, during a dc measurement, a dc signal to said dc field coil and measures dc magnetic characteristics of said sample, and
   (c) a computer connected to control said ac signal processing arrangement and said dc signal processing arrangement to perform said ac and dc measurements successively without requiring removal of said sample from said chamber; and
   a movable mechanical structure that retains said sample within said chamber and moves said sample relative to said sensor coil arrangement during said dc measurement.

19. A system as in claim 18 wherein said movable mechanical structure includes an electric motor controlled by said computer at least during said dc measurements.

20. A method for measuring ac and dc magnetic characteristics of a sample comprising the following successively performed steps:
   (a) disposing a sample within a chamber and magnetically coupling said sample to an ac field coil, a dc field coil and at least one sensing coil;
   (b) subsequently to said step (a), applying an ac signal to said ac field coil under computer control and measuring ac magnetic characteristics of said sample in response to signals received from said at least one sensing coil;
   (c) subsequently to said step (b), without removing said sample from said chamber, applying a dc signal to said dc field coil, moving said sample relative to said pickup coil under computer control, and measuring dc magnetic characteristics of said sample in response to signals received from said pickup coil; and
   (d) subsequently to said step (c), removing said sample from said chamber.

21. A system as in claim 20 wherein said disposing step sensor includes coupling said sample to a pair of balanced sensing coils, and each of said steps (b) and (c) comprises having a computer control an electric motor to move said sample relative to said pair of balanced sensing coils to obtain substantially symmetrical responses from each of said sensing coils.

22. A method for measuring ac and dc magnetic characteristics of a sample comprising the following successively performed steps:
   (a) disposing a sample within a chamber and magnetically coupling said sample to an ac field coil, a dc field coil and at least one sensing coil;
   (b) subsequently to..said step (a), applying a dc signal to said dc field coil, moving said sample relative to said at least one sensing coil under computer control, and measuring dc magnetic characteristics of said sample in response to signals received from said sensing coil;
   (c) subsequently to said step (b), without removing said sample from said chamber, applying an ac signal to said ac field coil under computer control and measuring ac magnetic characteristics of said sample in response to signals received from said at least one sensing coil; and
   (d) subsequently to said step (c), removing said sample from said chamber.

23. A system for measuring ac and dc magnetic characteristics of a sample, said system comprising:
   a chamber;
   a dc field coil;
   at least one non-superconducting sensor coil arrangement disposed within said chamber, said sensor coil arrangement including a non-superconducting ac field coil and two coaxial, oppositely wound non-superconducting sensing coils;
   electronics coupled to said dc field coil and to said sensor coil arrangement, said electronics comprising:
   (a) ac signal processing circuitry for, during an ac measurement, applying an ac signal to said ac field coil and measuring ac magnetic characteristics of said sample in response to signals received from said coaxial, oppositely wound sensing coils,
   (b) dc signal processing circuitry for, during a dc measurement, applying a dc signal to said dc field coil and measuring dc magnetic characteristics of said sample, and
   (c) a computer controller connected to at least in part control said ac signal processing circuitry and said dc signal processing circuitry, said computer controller controlling said system to successively perform said ac and dc measurements without requiring removal of said sample from said chamber; and
   a movable mechanical structure that retains said sample within said chamber and moves said sample relative to said sensor coil arrangement during said dc measurement, said computer controller automatically controlling said movable mechanical structure to move relative to said oppositely wound sensing coils during said dc measurement to provide substantially symmetrical outputs from said sensing coils.

24. A method for measuring ac and dc magnetic characteristics of a sample comprising the following successively performed steps:
   (a) disposing a sample within a chamber and coupling said sample to a non-superconducting ac field coil, a pair of coaxial, oppositely wound non-superconducting sensing coils, and a dc field coil;
   (b) subsequently to said step (a), applying an ac signal to said non-superconducting ac field coil under computer control and measuring ac magnetic characteristics of said sample in response to signals received from said pair of coaxial, oppositely wound non-superconducting pickup coils;
   (c) subsequently to said step (b), without removing said sample from said chamber, applying a dc signal to said dc field coil, moving said sample relative to said sensing coils under computer control, and measuring dc magnetic characteristics of said sample in response to signals received from said sensing coils; and
   (d) subsequently to said step (c), removing said sample from said chamber.

25. A method for measuring ac and dc magnetic characteristics of a sample comprising the following successively performed steps:
   (a) disposing a sample within a chamber and coupling said sample to a non-superconducting ac field coil, a pair of coaxial, oppositely wound non-superconducting sensing coils, and a dc field coil;
   (b) subsequently to said disposing step (a) applying a dc signal to said dc field coil, moving said sample relative to said pair of coaxial, oppositely wound non-superconducting sensing coils under computer control, and measuring dc magnetic characteristics of said sample in response to signals received from said sensing coils;
   (c) subsequently to said step (b), without removing said sample from said chamber, applying an ac signal to said non-superconducting ac field coil under computer control and measuring ac magnetic characteristics of said sample in response to signals received from said sensing coils; and
   (d) subsequently to said step (c), removing said sample from said chamber.

* * * * *